United States Patent
Easterbrook, III et al.

(10) Patent No.: US 6,238,334 B1
(45) Date of Patent: May 29, 2001

(54) METHOD AND APPARATUS FOR ASSISTING A HEART TO PUMP BLOOD

(75) Inventors: Willaim A. Easterbrook, III, Westwood, NJ (US); Ludmila Gudis, Timonium, MD (US); Mark S. Howansky, Union City; Howard R. Levin, Teaneck, both of NJ (US); Paul Michelman, New York, NY (US); Robert W. Reinhardt, Chatham, NJ (US); Craig W. Sherman, Arlington, MA (US); Joshua E. Tsitlik, Cliffside Park, NJ (US); Naum Ziselson, Baltimore, MD (US)

(73) Assignee: Cardio Technologies, Inc., Pine Brook, NJ (US)

( * ) Notice: Subject to any disclaimer, the term of this patent is extended or adjusted under 35 U.S.C. 154(b) by 0 days.

(21) Appl. No.: 09/185,287

(22) Filed: Nov. 3, 1998

Related U.S. Application Data

(60) Provisional application No. 60/064,086, filed on Nov. 3, 1997, and provisional application No. 60/098,130, filed on Aug. 27, 1998.

(51) Int. Cl.[7] .................................................. A61M 1/10
(52) U.S. Cl. ................................................ 600/16; 623/3.21
(58) Field of Search ........................... 600/16–18; 623/3, 623/3.1, 3.16, 3.21

(56) References Cited

U.S. PATENT DOCUMENTS

| | | |
|---|---|---|
| 2,826,193 | 3/1958 | Vineberg . |
| 3,034,501 | 5/1962 | Hewson . |
| 3,053,249 | 9/1962 | Smith . |
| 3,233,607 | 2/1966 | Bolle . |
| 3,279,464 | 10/1966 | Kline et al. . |
| 3,371,662 | 3/1968 | Held et al. . |
| 3,376,863 | 4/1968 | Kolobow et al. . |
| 3,455,298 | 7/1969 | Anstadt . |
| 3,478,737 | 11/1969 | Rassman . |
| 3,496,932 | 2/1970 | Prisk et al. . |
| 3,513,836 | 5/1970 | Sausse . |
| 3,587,567 | 6/1971 | Schiff . |
| 3,590,815 | 7/1971 | Schiff . |
| 3,613,672 | 10/1971 | Schiff . |
| 4,016,871 | 4/1977 | Schiff . |
| 4,048,990 | 9/1977 | Goetz . |
| 4,192,293 | 3/1980 | Asrican . |
| 4,314,550 | 2/1982 | Apstein . |
| 4,448,190 | 5/1984 | Freeman . |
| 4,506,658 | 3/1985 | Casile . |
| 4,536,893 | 8/1985 | Parravicini . |
| 4,621,617 | 11/1986 | Sharma . |
| 4,690,134 | 9/1987 | Synders . |
| 4,731,076 | 3/1988 | Noon et al. . |
| 4,809,684 | 3/1989 | Gardner et al. . |
| 4,846,831 | * 7/1989 | Skillin ...................................... 623/3 |

(List continued on next page.)

FOREIGN PATENT DOCUMENTS

| | | |
|---|---|---|
| 1499305 | 7/1967 | (FR) . |
| 457473 | 6/1973 | (SU) . |
| 984477 | 4/1981 | (SU) . |

Primary Examiner—Kennedy Schaetzle
(74) Attorney, Agent, or Firm—Darby & Darby

(57) ABSTRACT

A ventricular cuff is designed to assist a heart to pump blood by applying uniform pressure to a majority portion of an exterior ventricular surface of the heart. A heart engaging structure is preferably provided for releasably engaging the heart to hold the heart in place relative to the cuff. The ventricular cuff includes an outer shell, an inflatable inner bladder and a fastener assembly. The heart engaging structure and ventricular cuff define an upwardly opening chamber sized for receiving a heart. The bladder has an opening for communication with a source of fluid under pressure so that the bladder is cyclically inflated and deflated at a predetermined rate to assist the ventricles of the heart to properly contract.

47 Claims, 23 Drawing Sheets

U.S. PATENT DOCUMENTS

| | | |
|---|---|---|
| 4,922,893 | 5/1990 | Wright et al. . |
| 4,957,477 | 9/1990 | Lundback . |
| 5,098,369 | 3/1992 | Heilman et al. . |
| 5,119,804 | 6/1992 | Anstadt . |
| 5,131,905 | 7/1992 | Grooters . |
| 5,169,381 | 12/1992 | Snyders . |
| 5,256,132 | 10/1993 | Snyders . |
| 5,383,840 | 1/1995 | Heilman et al. . |
| 5,385,528 | 1/1995 | Wilk . |
| 5,429,584 | 7/1995 | Chiu . |
| 5,453,076 | 9/1995 | Kiyota et al. . |
| 5,533,958 | 7/1996 | Wilk . |
| 5,558,617 | 9/1996 | Heilman et al. . |
| 5,571,074 | 11/1996 | Buckman, Jr. et al. . |
| 5,713,954 | 2/1998 | Rosenberg et al. . |
| 5,738,627 | 4/1998 | Kovacs et al. . |
| 5,749,839 | 5/1998 | Kovacs . |
| 5,971,910 * | 10/1999 | Tsitlik et al. ............................ 600/16 |

* cited by examiner

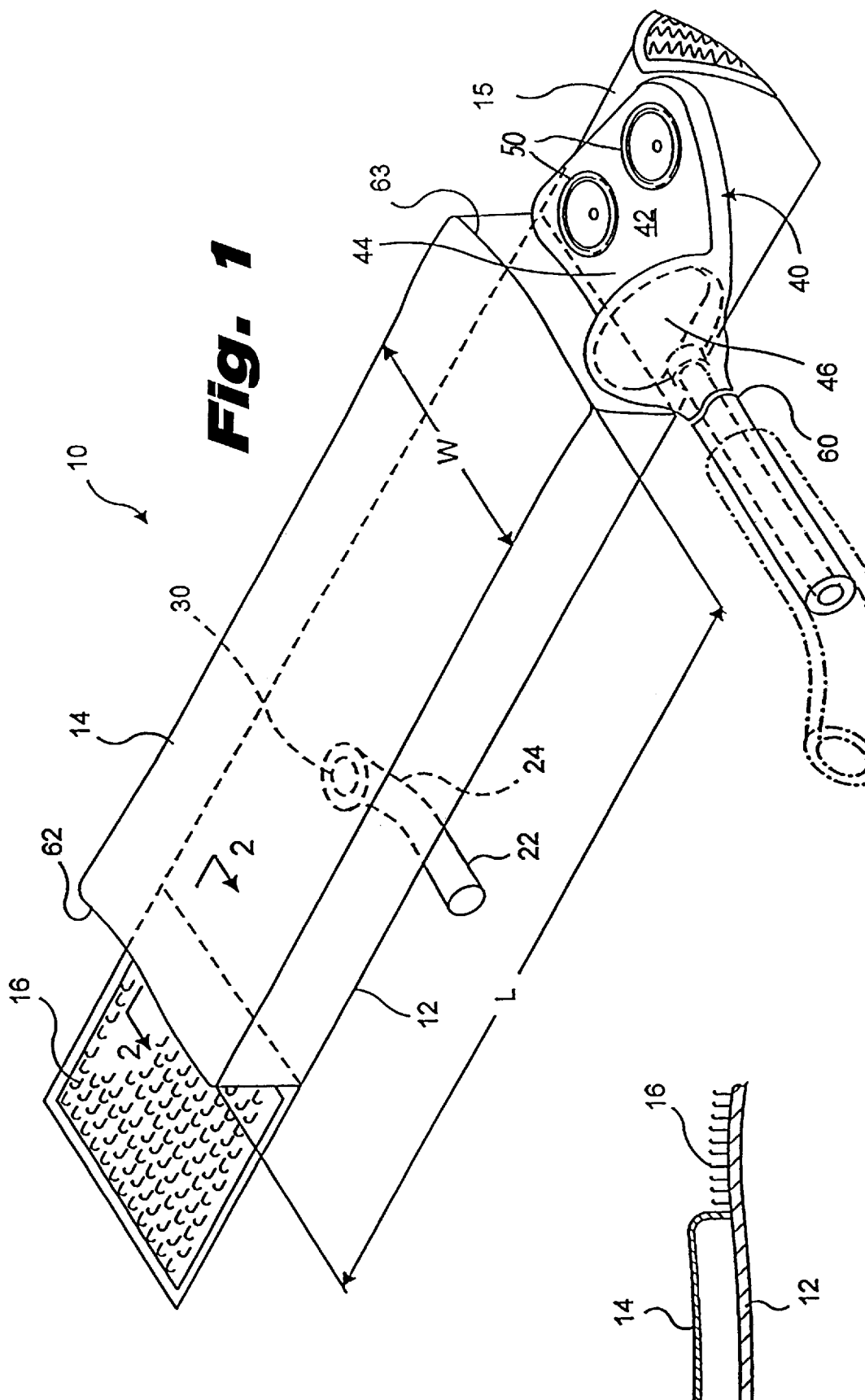
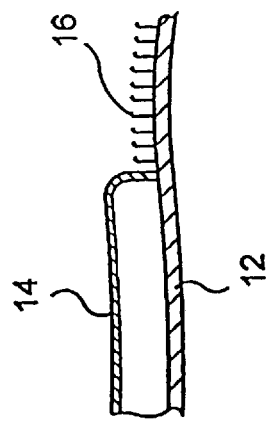

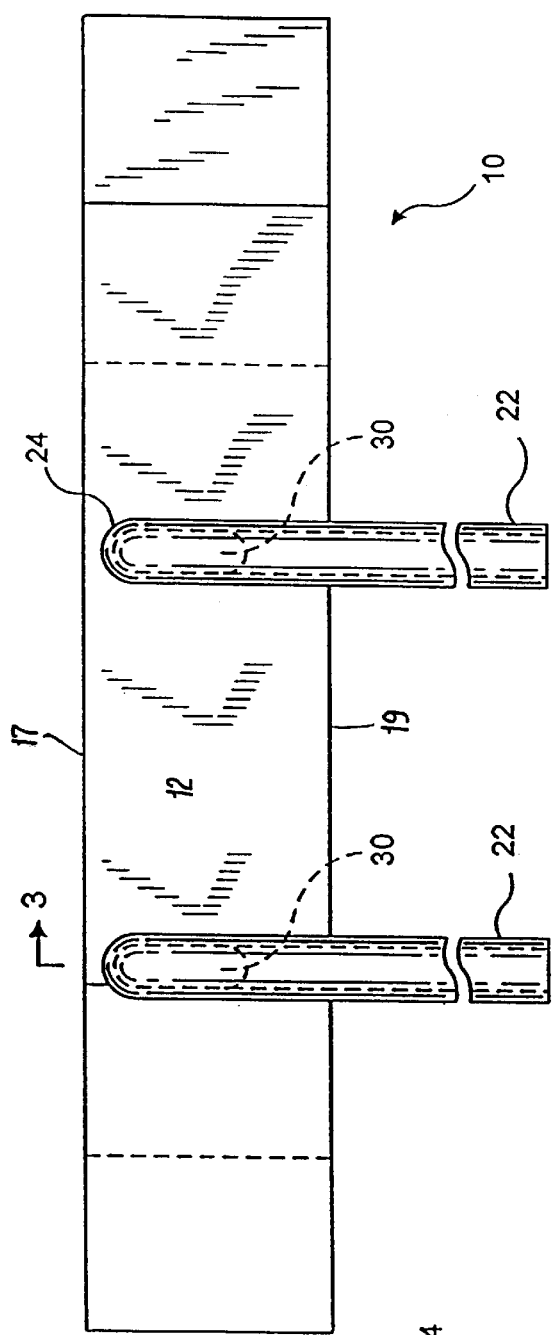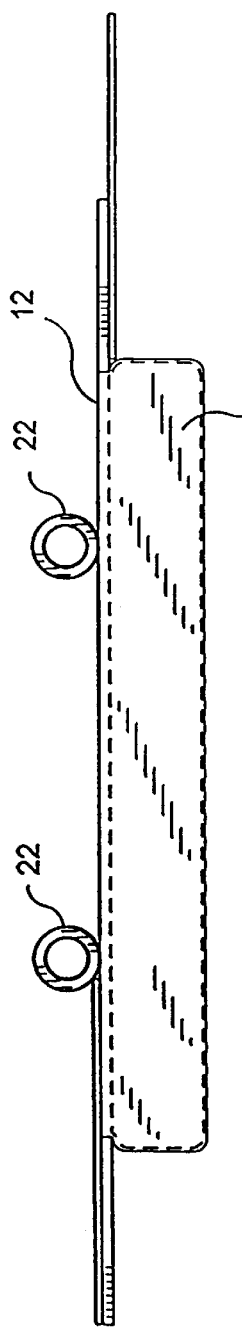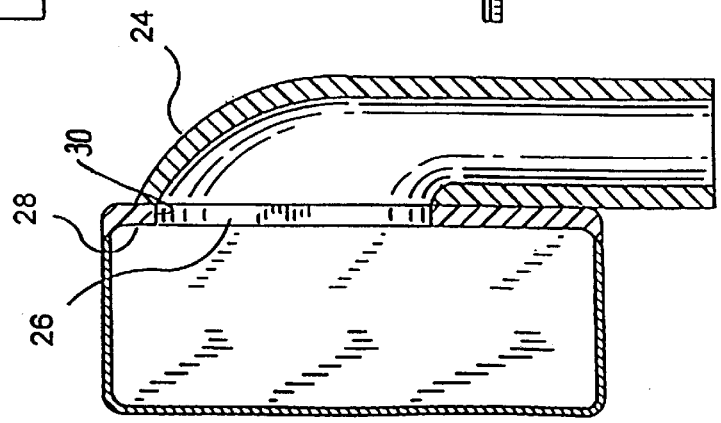

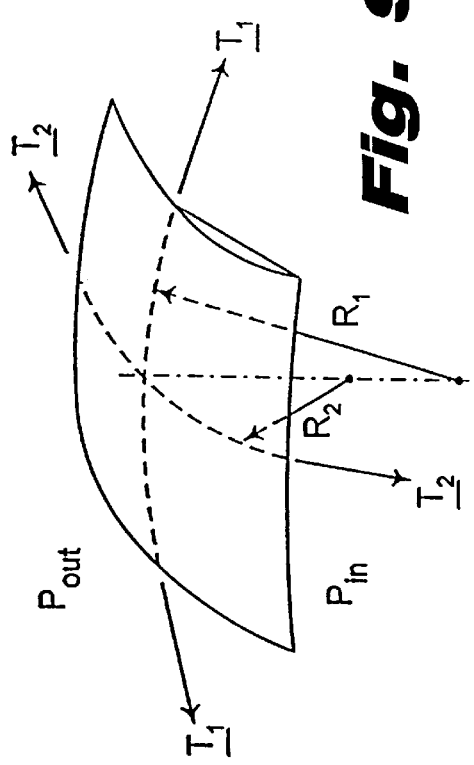
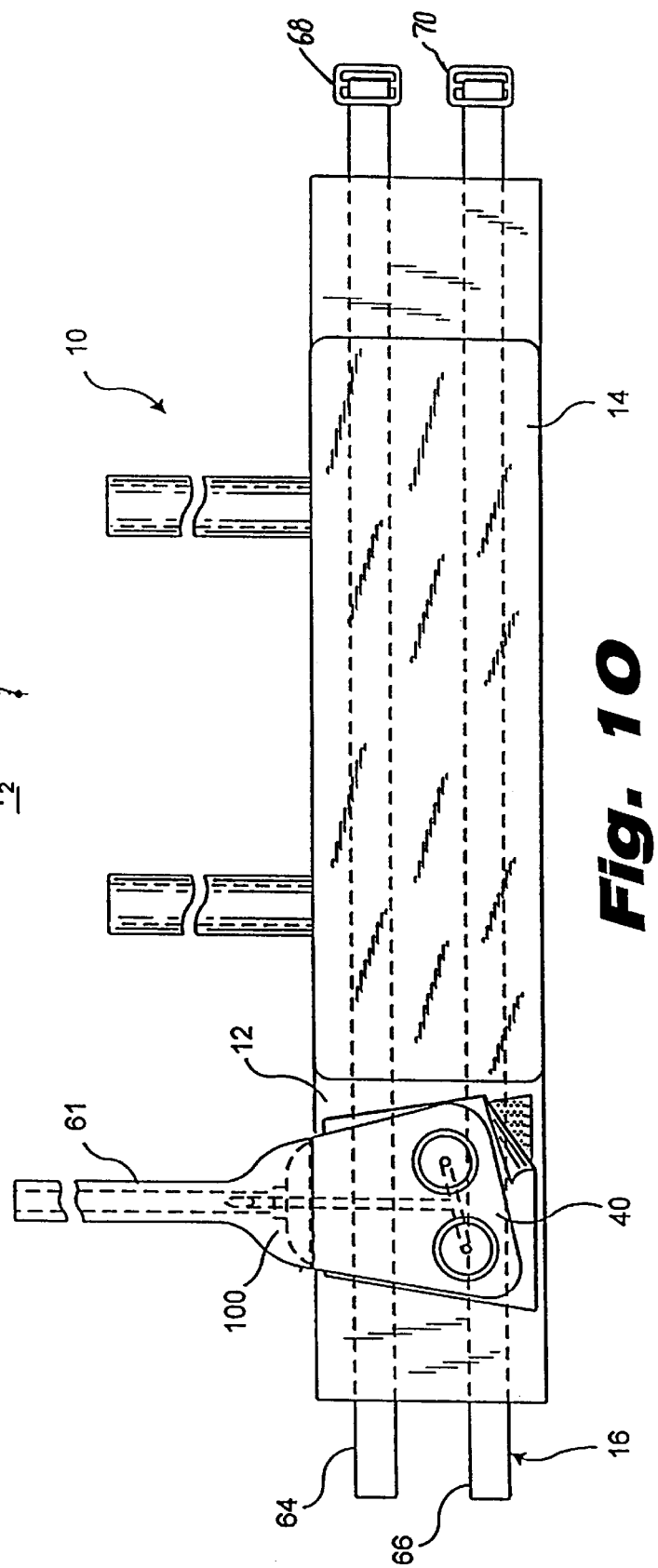

METHOD AND APPARATUS FOR ASSISTING A HEART TO PUMP BLOOD

This patent application claims the priority of U.S. provisional patent application No. 60/064,086, filed on Nov. 3, 1997, the entire disclosure of which is incorporated herein by reference and U.S. provisional patent application No. 60/098,130, filed on Aug. 27, 1998, the entire disclosure which is incorporated herein by reference.

BACKGROUND OF THE INVENTION

1. Field of the Invention

The present invention relates to temporary therapeutic devices to work in conjunction with a diseased or failing heart to satisfy the hemodynamic needs of a patient. More particularly, the invention relates to a ventricular cuff for assisting a heart to pump blood by intermittently applying pressure to at least a portion of the ventricular surface of the heart at predetermined intervals to aid the ventricles in properly contracting.

2. Discussion of the Related Art

The human heart is a very complicated organ that relies on both mechanical and electrical operation in order to properly perform. As with any complicated mechanism, problems can and do arise, and the heart is no exception. For example, over time the electrical pathways in the heart (which sequentially cause the atria and ventricles to contract) may fail, thereby causing the heart to lose its rhythm, which is known as arrhythmia. In that event, the ventricles will contract at improper times, and as a result the output of blood decreases. In addition, in some failing hearts the muscle of the heart no longer contracts the ventricles to a sufficient extent, also resulting in a dangerous reduction in the amount of blood flow.

Numerous attempts have been made to assist these diseased or failing hearts by applying external pressure directly to the heart. One such example is direct manual compression of the heart by a person's hand during open chest cardiopulmonary resuscitation. Often, however, the patient requires cardiac or circulatory support for extended periods of time, such as hours, days, or even weeks, and it is quite difficult for medical personnel to apply a rhythmic pulsating pressure for such an extended period of time. Further, it is difficult if not impossible to apply by hand a uniform compressing force to a significant portion of the exterior ventricle surface of the chamber of the heart. Moreover, the chest should not be opened for extended periods of time because of the increased risk of infection. As such, manual manipulation of the heart is not a solution to the problem in most cases.

To overcome this problem, mechanical devices have been developed to apply external pressure directly to the heart. Some of these devices utilize an inflatable liner that surrounds the heart. For example, U.S. Pat. No. 5,119,804 to Anstadt discloses a cup that is provided with an elastomeric liner. The heart is held in place within the liner, which is cyclically inflated and deflated to apply external pressure to the heart. While this device provides an improvement in hemodynamics for a diseased or failing heart, the device nevertheless suffers from shortcomings, one being the fact that only a fraction of the external fluid pressure that is applied in the cup inlet to displace the liner, which in turn displaces the heart wall, is transmitted to the heart itself to assist in pumping blood. As the liner is inflated and stretched, a transmural pressure is created in the liner. The transmural pressure in the liner is the difference in pressure that is applied to both sides of the liner. In other words, the transmural pressure is the pressure within the liner that is generated by the elastic wall tensions of the liner. As illustrated in FIG. 9 and described in *Augmentation of Pressure In A Vessel Indenting the Surface of the Lung*, 1987, by Joshua E. Tsitlik, et al. the transmural pressure ($P_{tm}$) for a stretched liner is:

$$P_{tm} = P_{tm} - P_{out} = T_1/R_1 + T_2/R_2$$

where the radii $R_1$ and $R_2$ are the maximum and the minimum radii of the membrane curvature, respectively, i.e., the principal radii of curvature. The vectors $T_1$ and $T_2$ are the elastic wall tensions (the force per unit length) acting along the edges of the surface element.

In practice, as the liner is inflated, because of its axial length limitation, it stretches and bulges radially inwardly. Thus, the transmural pressure of the liner is directed in the radially outward direction (i.e., away from the heart), such that the pressure applied to the heart is less than the pressure applied to the liner. In addition, due to the bulging of the liner, the heart is deformed into a generally hour-glass shape. In other words, the outer central portions of the ventricles of the heart are deformed inwardly from their normally convex shape into concave shapes (i.e., the heart is indented). Thus, there is not a uniform application of pressure to the outer walls of the ventricles. In addition, a transmural pressure of the indented portion of the heart wall is directed in the radially outward direction and, thus, is subtracted from the fluid pressure that is applied by the liner to the outer surface of the heart. Thus, this transmural pressure is also subtracted from the fluid pressure that is applied within the liner. In other words, the heart wall itself is fighting against the externally applied force. Thus, the externally applied force in devices such as that disclosed in Anstadt does not cooperate with the heart's own natural compressive forces during the systolic phase. It actually fights against the heart's natural motion even when the pressure is applied in synchrony with the natural systolic phase of the heart. As a result, the fluid pressure applied within the liner must overcome the transmural pressure created both in the liner and in the heart wall. Therefore, a relatively high pressure must be applied within the liner (e.g., 150–200 mm Hg) to achieve assistance in circulation support.

Thus, the prior art devices suffer from the further shortcoming that they apply pressure to the heart in a nonuniform manner. Such liners are made from a silicone rubber elastomer, which, when inflated, are inherently distended and assume an inwardly convex shape (as shown in FIG. 9 of the '804 Patent). As a result, those devices cause the heart to indent in its center portion, while allowing the heart ventricles to remain expanded at their upper and lower portions. Therefore, the prior art devices inefficiently assist in pumping blood to and from the heart. As a result, substantial pressure needs to be applied to the inner side of the liner (i.e., $P_{in}$) to effectuate displacement of the blood from the ventricles. A considerable portion of the pressure that is applied to the inner side of the liner is wasted because, as described above, transmural pressure is created in the liner and the heart wall.

Another shortcoming inherent in the prior art devices results from the fact that relatively high pressures are applied almost exclusively to the central portion of the ventricles' outer surfaces. This causes the heart to deform into an unnatural shape and may even eventually cause trauma (e.g., bruises) to the heart, especially if one of those devices is operated for an extended period of time.

Several prior art devices apply a vacuum pressure to a relatively small area in the lower portion of the cup to prevent the heart from being ejected from the cup during the systolic compressing phase. The application of a relatively large vacuum to such a small surface of the heart, especially in view of the large external force that needs to be applied to perform the holding function, causes further trauma to the heart.

SUMMARY OF THE INVENTION

The ventricle portion of the heart normally has an outer convex shape during both the systolic and diastolic phases. The present inventors have surprisingly discovered that if a portion of the ventricles are assisted with an externally and uniformly applied force during the systolic phase, a significant increase in the amount of fluid being pumped by the heart can be achieved compared to the same force being applied in a non-uniform manner. This is due to the fact that in the present invention the pressure applied to the heart surface and the pressure generated by contracting the heart wall add up to produce higher pressures in the ventricles without additional oxygen consumption by the ventricular wall. Therefore, by the non-distorting compression of the heart, the present invention assists the heart in generating higher blood pressure and blood flow while utilizing low and safe compression pressures.

Thus, it is an object of the present invention to provide a ventricular cuff for efficiently assisting the mechanical compression of the heart, especially during the systolic phase. It is another object to operate such a ventricular cuff without unduly deforming the natural shape of the heart during the mechanical compression of the heart.

It is a further object of the present invention to provide a ventricular cuff for assisting heart function, which applies substantially uniform fluid pressure against the exterior surface of at least a portion of the ventricular portion of the heart during the systolic phase.

It is yet a further object of the present invention to provide a ventricular cuff for assisting a heart function that can be installed in its operative position with minimal movement of the heart.

It is a further object of the present invention to provide a ventricular cuff that applies a vacuum holding force over a relatively large surface area of the heart. It is still a further object of the present invention to provide a device that applies a vacuum holding force in such a manner so as to cause considerably less trauma to the heart.

The above-mentioned and other objects are satisfied by the present invention, which in one illustrative embodiment is directed to an apparatus for assisting a heart to pump blood, including: an inflatable bladder, the bladder being inflatable to assume a heart contracting position; a suction membrane configured to make a close fit over at least a portion of the heart, the suction membrane defining an interior chamber to receive at least a portion of the heart therein; a suction line in communication with the interior chamber of the suction membrane, the suction line being operative to create a vacuum in the chamber to draw the suction membrane inwardly into engagement with the heart; and an inlet line connected for communication with the bladder, the inlet line serving to selectively deliver pressurized fluid to and withdraw pressurized fluid from the bladder.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings wherein:

FIG. 1 is a perspective view of a ventricular cuff according to one embodiment of the present invention;

FIG. 2 is a partial sectional view of the ventricular cuff shown in FIG. 1 and taken along the line 2—2 of FIG. 1;

FIG. 3 is a sectional view taken along lines 3—3 of FIG. 4 and looking in the direction of the arrows;

FIG. 4 is a bottom plan view of the ventricular cuff shown in FIG. 1;

FIG. 5 is a side view of the ventricular cuff shown in FIGS. 1 and 4;

FIG. 9 is a schematic illustration of a curved differential surface element of stretched liner wall according to prior art liner devices;

FIG. 10 is a top plan view of an alternate embodiment of a ventricular cuff according to the present invention;

DETAILED DESCRIPTION OF THE PREFERRED EMBODIMENTS

Figure 6:
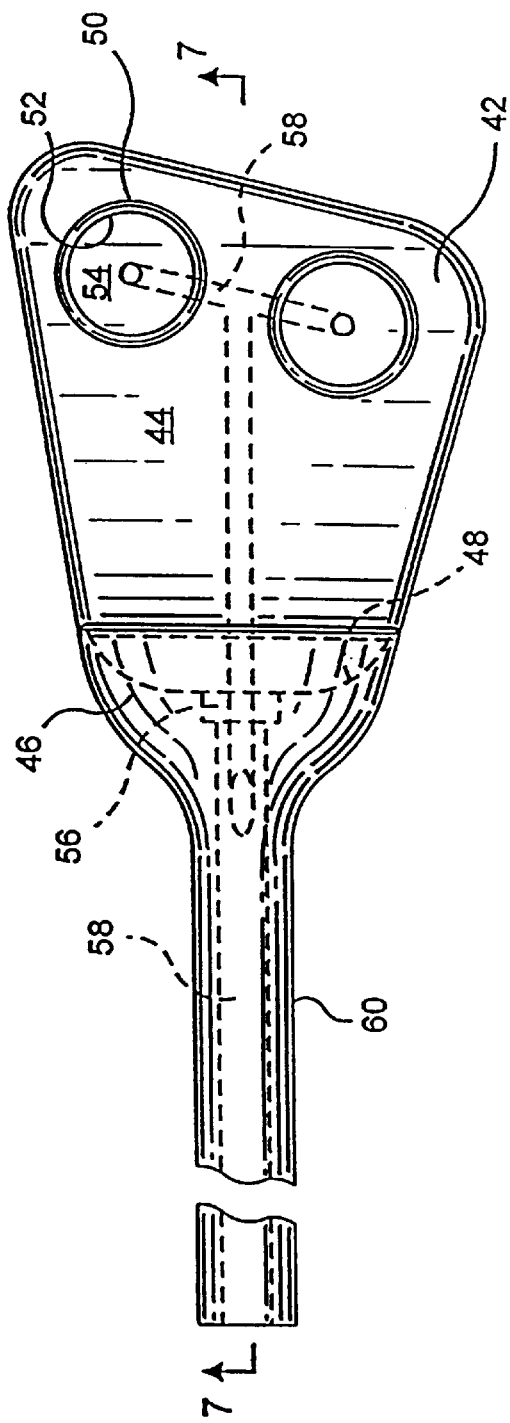
FIG. 6 is a top plan view of a suction anchor included in the ventricular cuff of FIG. 1.

Referring now to FIG. 1, one illustrative embodiment of a ventricular cuff 10 is shown. The ventricular cuff 10 is preferably controlled in such a manner that it is inflated and deflated at a predetermined and controllable rate in concert with the patient's heart beat. The cuff includes a bladder 14 that is inflated and deflated at controlled rates so that the bladder selectively compresses directly against the patient's heart and thereby assists in compressing the ventricles to pump blood through the patient's circulatory system.

The ventricular cuff 10 of the present invention, in one illustrative embodiment, is designed to fit around the human heart, more specifically around the ventricles of the heart, in a manner similar to that by which a blood-pressure cuff is fitted to a patient's arm during the measurement of the patient's blood pressure. As shown in FIGS. 1 and 2, the ventricular cuff 10 generally comprises three main elements, an elongated outer shell 12, the inflatable inner bladder 14, and a fastener assembly 16. The fastener can take many different forms, such as a conventional mushroom-head fastener, or a hook and loop-type nylon fastener (e.g., VELCRO®), a hook and eye fastener, or any other well known fastener.

The outer shell 12 is preferably made from a substantially non-stretchable, yet foldable and bendable material so that it may easily conform to the outer shape of a heart. The material used is preferably plastic and is attachable to itself at its ends to assume an annular configuration by using the fastener assembly 16 as described above. The material is impervious to fluids including the inflation fluid (e.g., air), and preferably resists elongation (in one illustrative embodiment, the material is chosen such that it does not elongate more than about 2% of its length when the pressure inside the cuff is 200 mm Hg higher than atmospheric pressure located outside the cuff). Alternatively, a material with a higher percentage elongation property may be used.

As shown in FIGS. 1 and 2, the cuff 10 is generally rectangular having, in one exemplary, non-limiting, embodiment for a dog heart from a mongrel dog, weighing about 22 kg, an approximate overall length L of about 330 mm, a width W of approximately 70 mm and an inflated depth of about 30 mm. Unlike a conventional bloodpressure measuring cuff, the ventricular cuff, according to one embodiment of the present invention, includes a substantially flat side 15 to be disposed under a suction anchor 40 (described below), which allows the cuff to better conform to the specific shape of a human heart. The fastener assembly 16 is disposed at the respective ends of the cuff 10, is about 50 mm long, and is supported or backed by the outer shell 12.

The dimensions of the inflatable bladder 14 are preferably determined based on the size, including the circumference, of the heart to be assisted. Adult human hearts are typically on the order of about 300 mm in circumference (up to about 400 mm for diseased hearts) and, therefore, the length L of bladder 14 should be at least this long minus the width of the flat side 15, which corresponds to the width of the relatively flat posterior, inferior side of the heart. It will be understood that various different sizes of bladders may be designed to accommodate patients with different sized hearts. In addition, the fastener assembly provides a degree of adjustment to accommodate different sized hearts. Bladder 14 preferably has a width W that corresponds to the distance from the inferior vena cava on the posterior inferior side of the heart to the apex of the heart. On the anterior superior side of the heart, the upper limit for determining the width W of bladder 14 is the AV groove, while the apex of the heart is still the lower limit. For most adult human hearts a width W of between 60–80 mm, and typically about 70 mm, will work effectively without compressing the atrial portion of the heart. Bladder 14 is formed integrally with outer shell 12 so that outer shell 12 forms one air-tight wall of the bladder 14 (FIG. 2). In addition, the bladder 14 preferably does not extend over fasteners 16, as shown in FIG. 2.

As shown in FIGS. 1, 3, 4 and 5, the ventricular cuff 10 includes at least one and preferably multiple air supply conduits 22 that provide fluid communication between a supply of pressurized gas (not shown) and the inflatable bladder 14. Air supply conduits 22 are preferably made of a material that resists kinking when the tube is bent and resists collapsing when external pressure is applied to the tubing, such as a wire reinforced rubber/plastic tubing, for example tygon, silicon, etc., and have an inner diameter of no less than approximately 3/16 inches. Air supply conduits 22 should be capable of supplying gas pressures of 300 mm Hg with preferably no more than a 2% increase in inner diameter. However, if the supply conduit increases by greater than 2%, then a greater volume of fluid will be required. Air supply conduits 22 preferably include curved ends 24 (as shown in FIG. 3) that define an opening 26, which includes a rim 28. Rim 28 of air supply conduit 22 is connected to the outer shell 12 in any suitable manner. An inlet opening 30 is formed within outer shell 12, within the area defined by the adhered rim 28. The resulting air supply conduit 22 is attached to cuff 10 so that conduit 22 lies generally parallel or flat with respect to outer shell 12, providing a relatively low-profile structure.

Bladder 14 is, in a preferred embodiment, made from a substantially fluid impermeable film (i.e., substantially unyielding and non-stretchable) that is reinforced by a tear-resistant, non-stretchable, preferably woven, material. In one illustrative embodiment, bladder 14 is made from polyurethane (e.g., BioSpan®, Carbothane®, or the like), which is reinforced by a non-stretchable material, for example polyester. Thus, the bladder is made of non-stretchable, biocompatible, drapeable material that will not create a transmural pressure when inflated.

Of course, other materials that are of sufficient flexibility to permit the material to completely conform to the outer dimensions of an object placed within the device and apply substantially uniform pressure to the object (i.e., having good drapeability), without creating a transmural pressure within the material may be used. For example, if the material is sufficiently thin (for example, having a thickness of 0.5 mm or less), bladder 14 may be made from an elastic material such as, for example, silicone rubber or polyurethane. Bladder 14 could be made of a polyethylene terephthalate ("PET") material having a thickness from 0.01–0.02 mm and more preferably about 0.013 mm (i.e., 0.5 mil). Other examples of acceptable materials include, but are not limited to, polytetrafluoroethylenes ("PTFEs"), vinyl chloride-vinylidene chloride copolymers (e.g., SARAN WRAP®), polyurethane and any other fluid-impermeable, biocompatible material that will not create a transmural pressure when inflated.

The distance between outer shell 12 of cuff 10 and the surface of the heart may vary up to about 3–4 cm over the length of cuff 10 due to the non-uniform shape of the heart. The distance between outer shell 12 and the surface of the heart may change by as much as 2 cm during a cardiac cycle. During the cardiac cycle, as the ventricles re-fill with blood, they expand. This ventricular expansion displaces the inner wall of the bladder 14 radially outwardly toward the outer shell 12. It is important that bladder 14 be made to accommodate this ventricular expansion without resistance.

Although a specific size of cuff 10 was described above, many different sizes may be provided to accommodate various sizes of hearts.

It is preferred that cuff 10 be collapsible and sufficiently small to be inserted into the thoracic space through an approximately 7 cm left thoracotomy.

In one embodiment, the ventricular cuff 10 includes a suction anchor 40 (FIGS. 1 and 8) that is operative to prevent the heart from being extruded from the top end of cuff 10 during cuff compression. The suction anchor includes a paddle 42 with a flat surface 44 defining a pair of spaced apart suction ports 50. The suction anchor is placed against the flat side 15 of the cuff before it is wrapped around a heart. The suction anchor 40 could also be, for example, sewn or bonded to cuff 10 to securely connect the two together. The bladder 14 extends from a first end 62 to a second end 63, as illustrated in FIG. 1. When bladder 14 is inflated, it is not disposed underneath suction anchor 40. Thus, when cuff 10 is placed about the ventricles of a heart it essentially forms a D-shape in cross section with the flat portion of the D being formed by surface 44 of paddle 42.

In one illustrative embodiment, suction anchor 40 is spatula-shaped including the generally flat paddle 42 which gradually tapers to an integrally formed generally conical cup 46. The contact surface 44 of the paddle is sized and shaped to conform to the posterior inferior surface (i.e., "flat side") of the human heart. Cup 46 includes a receiving surface 48 that is sized and shaped to snugly receive the apex of the heart. At least one suction port 50 (preferably two) is located on contact surface 44 of paddle 42. Suction port 50 includes a circular raised soft sealing rim bead 52 defining a recess 54. Similarly, cup 46 includes a suction port 56 and a soft sealing rim 57 to define a recess.

Figure 7:
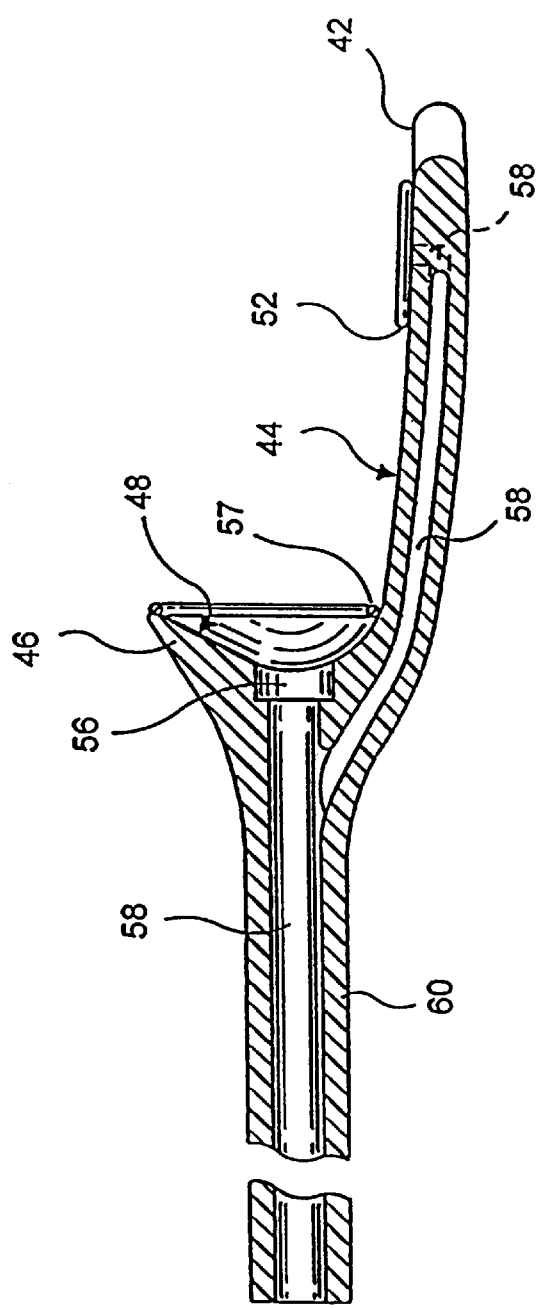
FIG. 7 is a cross-sectional side view of the suction anchor of FIG. 6.

Suction anchor 40 includes a suction conduit 58 connected to a vacuum source (not shown) that provides suction (negative pressure) to suction port 56 of cup 46 and to the one or more suction ports 50 of paddle 42, to thereby draw the heart into positive engagement with the respective rims 52 and 57. It is preferred that suction conduit 58 is formed integrally with cup 46 and paddle 42, as shown in FIGS. 6 and 7, and further defines a handle portion 60 which may assist a surgeon in positioning suction anchor 40 below and adjacent to the heart with minimal movement of the heart. The paddle 42, cup 46, and handle 60 are preferably integrally formed from a bio-compatible plastic.

Figure 8:
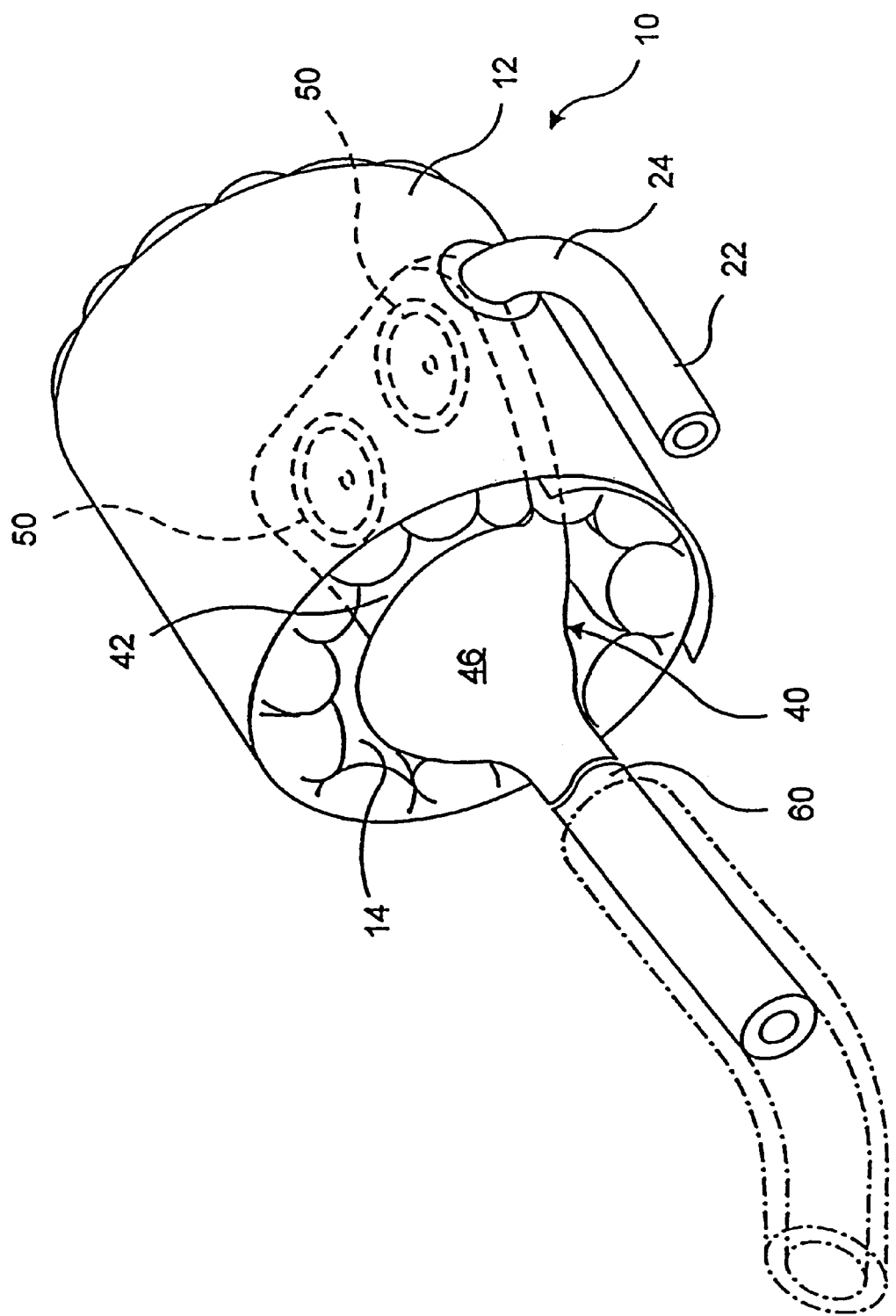
FIG. 8 is a perspective view of the ventricular cuff and suction anchor assembled together and configured for placement about a heart.

The operation of the apparatus according to one embodiment of the present invention will now be described with reference to FIGS. 1 and 8. The cuff 10 and suction anchor 40 are carefully positioned, in the open or unfastened position (see FIG. 1) so that suction anchor 40 snugly receives the apex of the heart and surface 44 of the paddle 42 contacts the relatively flat posterior inferior side of the heart. An upper edge 17 of cuff 10 is located just below the valve plane of the heart (e.g., below the inferior vena cava and below the AV groove). Lower edge 19 of cuff 10 may extend below the apex of the heart, but is preferably positioned adjacent to or just above the apex. Cuff 10 is now properly positioned about the heart by closing the cuff into a loop and connecting fasteners 16 at each end of the cuff to assume a generally annular configuration (see FIG. 8). When the cuff is wrapped around the heart, the material of the bladder forms a number of folds which allow the bladder to be displaced radially inwardly when inflated without requiring the bladder to stretch (FIG. 8).

A vacuum source (not shown) is then fluidly connected to suction conduit 58 to assist in holding the heart to cuff 10. Negative pressure draws heart tissue against the suction ports 50 of paddle 42 and suction port 56 of cup 46, which holds the suction anchor 40 in place with respect to the heart. A pulsating fluid pressure is transmitted through inflation conduits 22 to cyclically inflate and deflate bladder 14. An appropriate inflation/deflation drive system for carrying out this task is disclosed in U.S. Provisional Patent Application Serial No. 60/044,460, entitled Drive System For Controlling Cardiac Compression filed on Apr. 4, 1997, the rights to which have been assigned to the assignee of the rights to the present invention, and the disclosure of which is hereby incorporated by reference. The maximum fluid pressure is preferably 50–100 mm Hg above atmospheric pressure, and the minimum fluid pressure is preferably −50 to −100 mm Hg below atmospheric pressure. However, for resuscitation (i.e., the heart is not beating), the maximum fluid pressure is preferably about 150 mm Hg. During diastole, the air pressure within bladder 14 should be reduced as quickly as possible to prevent cuff 10 from impeding the refilling of the ventricles of the heart.

As fluid pressure increases within bladder 14, bladder 14 initially at least partially unfolds to conform to the exact shape of the portion of the heart not resting on the suction anchor 40 and, thereafter, applies a uniform pressure P to the entire external surface of the ventricles of the heart that is in contact with the bladder 14.

As discussed above, bladder 14 is made of a material which does not create a transmural pressure even when pressure is applied therein. In other words, the pressure applied to the exterior ventricular surface of the heart is essentially the same as the pressure within the bladder. Thus, as pressure within the bladder increases to the predetermined maximum pressure, the heart is compressed substantially uniformly such that the normally convex outer shape of the heart is maintained during the pressurized (i.e., systolic) cycle. Thus, the pressure of the heart wall upon the blood volume contained within the ventricles is directed in the radially inward direction and, thus, is added to the fluid pressure applied within the bladder 14. Thus, the bladder works with the heart wall, not against it, in applying pressure to the volume of blood within the ventricles. Therefore, the present invention assists the heart to generate pressure within the ventricles.

Because no transmural pressure is created in bladder 14 and the pressure exerted by the heart wall is cumulative, substantially lower fluid pressures can be utilized to obtain even better hemodynamics than compared to prior art systems. Using substantially lower driving fluid pressures considerably decreases the risk of causing trauma to the heart. Additionally, because lower driving pressures are utilized, a pneumatic or hydraulic driving system can be used, which has a relatively small size and complexity due to the reduced gas or liquid pressure requirements.

Preferably, fluid pressure is not applied against the atrial portion of the heart because the atrial portion of the heart is disposed above or outside of cuff 10. Additionally, bladder 14 does not directly apply fluid pressure against any portion of the heart that is supported by the suction anchor 40. Of course, during the compressive phase, the bladder 14 applies fluid pressure to the ventricular portion of the heart not resting on the suction anchor 40.

The timing for applying the pulsating fluid pressure is preferably synchronized with the natural timing of the heart's systolic and diastolic phases.

Once the systolic phase is complete, the fluid pressure transmitted through the conduits 22 are reduced in a controlled manner to initiate the diastolic phase, as is well known in the art. When the predetermined minimum pressure is reached within the bladder 14, at which time no pressure is applied to the exterior of the ventricular walls of the heart, the bladder 14 may still conform to the exterior shape of the heart, or if the minimum pressure is negative, the bladder 14 may withdraw to the interior walls of the outer shell 12. Thereafter, the systolic and diastolic phases continue in alternating fashion for as long as needed. Once the device is no longer needed to aid in assisting the heart to pump blood, the connection of the pulsating fluid pressure source to the inflation conduits 22 can be disconnected and the connection of the vacuum source to suction conduit 58 can also be disconnected. The cuff can then be removed from the heart and from the patient's chest cavity.

The pressure fluid supplied to and removed from conduits 22 is preferably a pneumatic fluid, such as, for example, air, carbon dioxide or an inert gas (e.g., argon). Alternatively, the pressure fluid may be a hydraulic fluid, such as, for example, water or saline.

Figure 11:
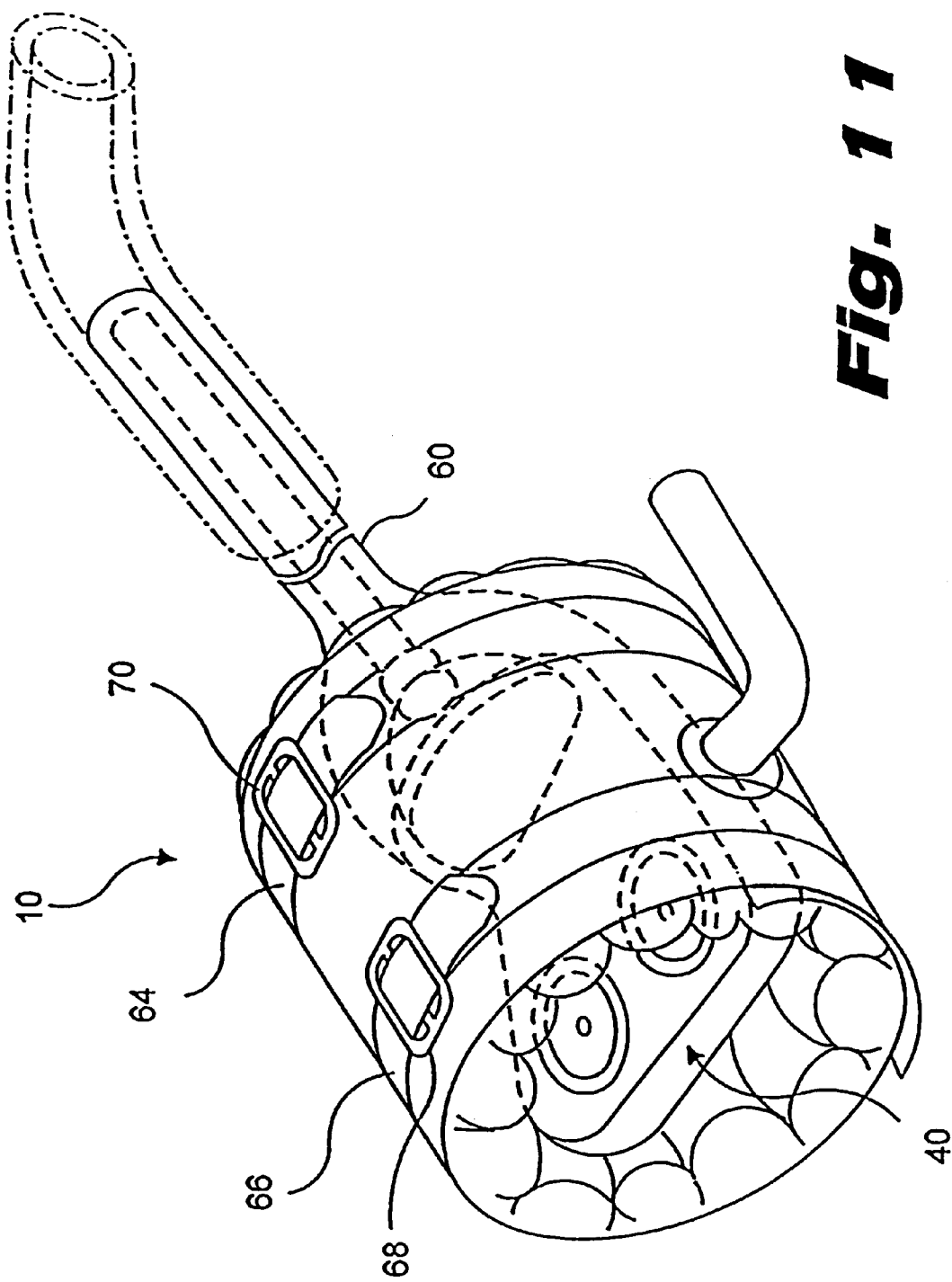
FIG. 11 is a perspective view of a ventricular cuff having a pair of expansion restricting belts placed about the cuff.
Figure 16:
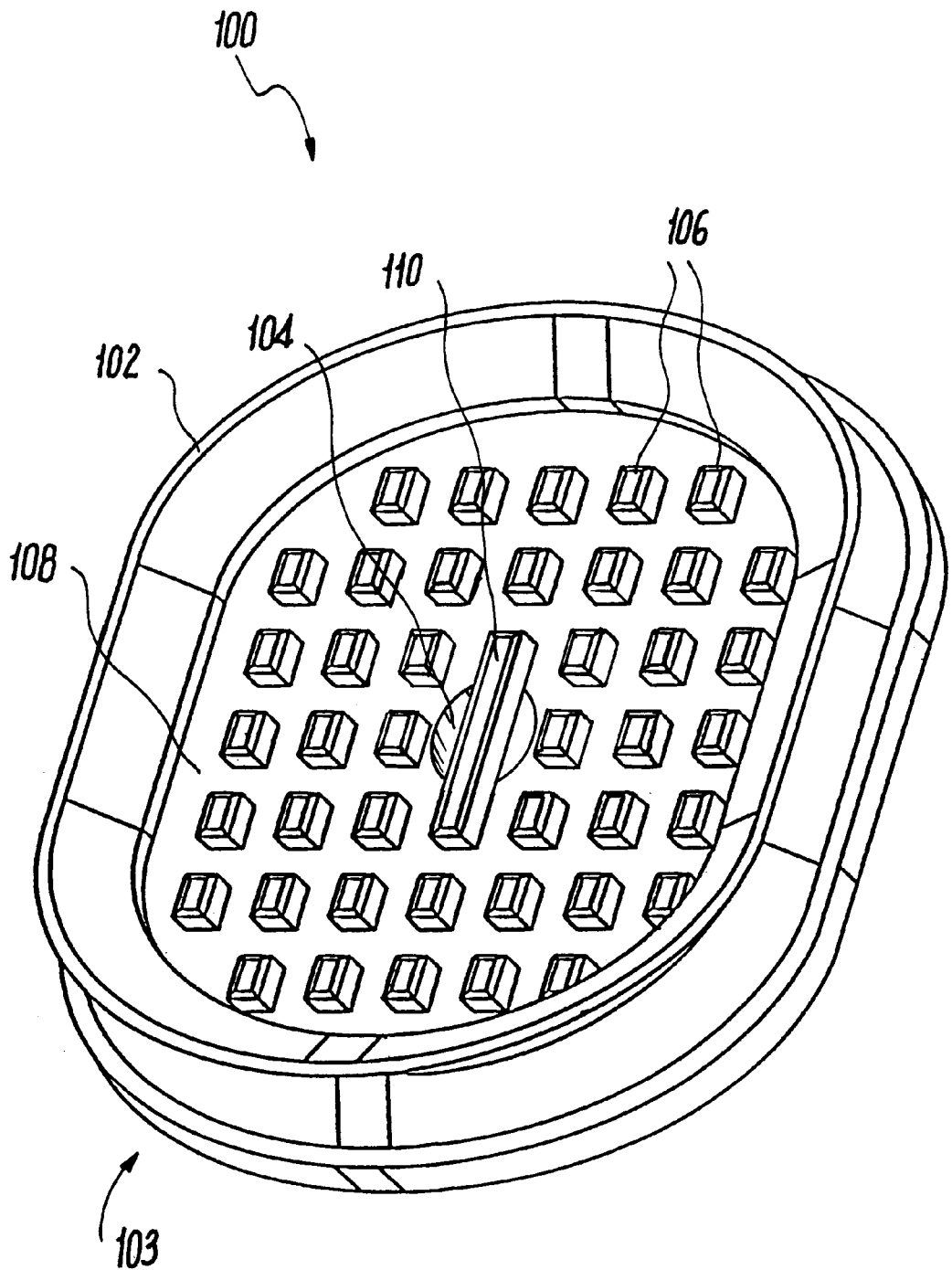
FIG. 16 is a perspective view of a suction pad according to one embodiment of the present invention.

Referring now to FIG. 10, another illustrative embodiment of the cuff 10 is shown. Cuff 10 includes a suction anchor 40 that is integral with outer shell 12. Suction anchor 40 is preferably formed as a suction cup 100 as illustrated in FIG. 16 and described below. A fastener assembly 16 is disposed on the underneath surface of suction anchor 40 and on the upper surface of a second end of cuff 10. A bladder 14 is disposed between suction anchor 40 and the fastener 16 that is disposed on the upper surface of the second end of cuff 10. Cuff 10 can be wrapped into the closed position as illustrated in FIG. 11 and is maintained in this position by the connection of fasteners 16. To prevent outer shell 12 from expanding, especially during the inflation of bladder 14, a pair of expansion restricting belts 64, 66 can be looped about cuff 10 and fastened in a predetermined position by buckles 68, 70, respectively. Buckles 68, 70 can be conventional mushroom-head fasteners, VELCRO® fasteners, or even the type of fastener that is conventionally used to fasten the belts in an airplane seat (of course, on a much smaller scale) so that the fastener will only permit the belt to be tightened without tightening the other. As bladder 14 is inflated, the outer circumference of outer shell 12 is limited by the fastened closed belts 64, 66. Thus, the pressure being applied by the inflated bladder 14 can be essentially directed entirely against the ventricles.

Figure 12:
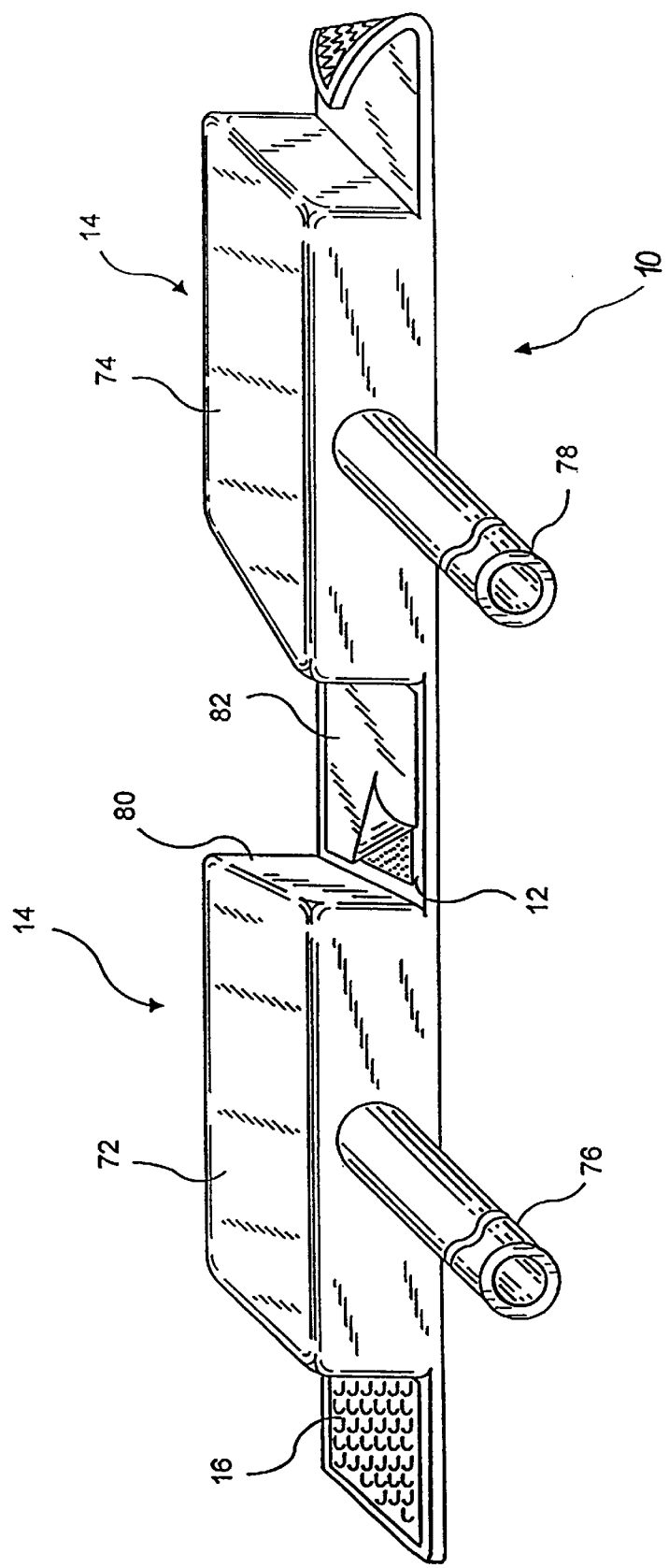
FIG. 12 is a perspective view of an alternate embodiment of a ventricular cuff according to the present invention.
Figure 13:
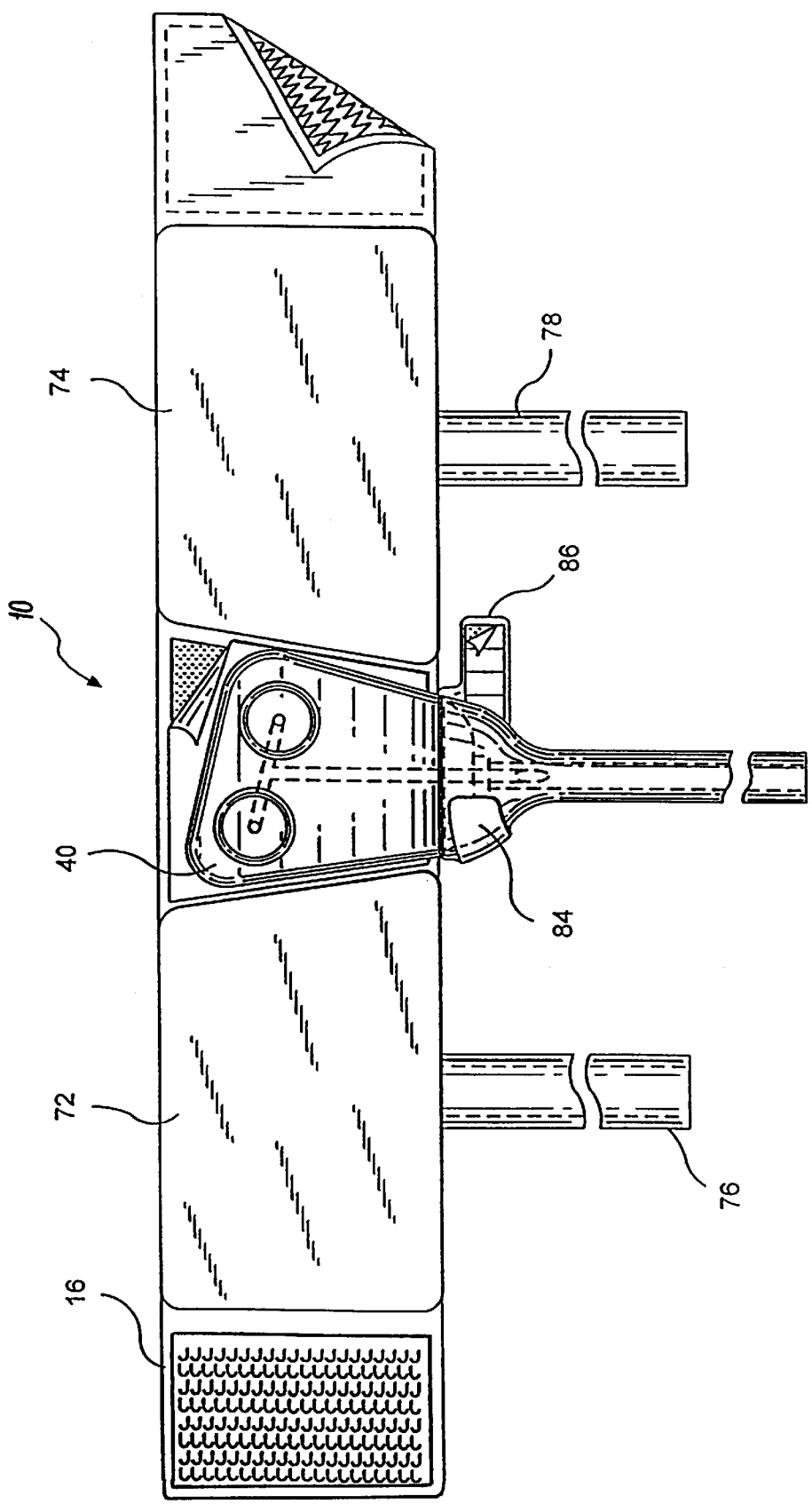
FIG. 13 is a top plan view of the ventricular cuff of FIG. 12 and having a suction anchor connected thereto.

Referring now to FIGS. 12 and 13, an alternate embodiment of cuff 10 is illustrated. In this embodiment the bladder 14 is divided into two spaced apart and separately inflatable sections 72, 74. Each section 72, 74 of bladder 14 is connected to an air supply conduit 76, 78 to provide fluid communication between an inflation gas supply (not shown) and the bladder. A fastener assembly 16 is again mounted at an upper surface at one end of cuff 10 and at an underneath surface at the opposite end of cuff 10 so that cuff 10 may be looped in the closed position and maintained in this position upon the fastening of fastener 16. Disposed between bladder 72 and 74 is a U-shaped channel 80, which is sized to receive suction anchor 40. The upper surface 82 of outer shell 12 may be provided with a fastener, such as, for example, an adhesive that is provided with a removable covering sheet. Fastener 82 may also be a Velcro attachment or a mushroom-head attachment or any other suitable fastener that are known to those skilled in the art.

FIG. 13 illustrates suction anchor 40 being temporarily connected to surface 82 by a pair of clamps 84, 86. By permitting suction anchor 40 to be selectively connected to cuff 10, the user can ensure that the relative position of suction anchor 40 with respect to cuff 10 is in the optimum position for the heart that the cuff is to be placed about.

In operation, the user will first place cuff 10, without suction anchor 40, under the heart with the cuff in the open position as illustrated in FIG. 12. The cuff can then be closed about the heart to form a loop and is maintained in this position by fastener 16. If desired, belts 64, 66 (see FIGS. 10 and 11) may be used to further maintain the position of cuff 10 about the heart. The user will then slide suction anchor 40 between the relatively flat inferior posterior surface of the heart and surface 82 in the desired optimum position. The user can then clamp suction anchor 42 to surface 82 through the use of clamps 84, 86. The now-connected assembly of the cuff 10 and suction anchor 40 can be removed, with minimal movement of the heart. Thereafter, suction anchor 40 can be secured to surface 82 via the use of the fastener (e.g., mushroom-head, adhesive, Velcro, etc.). This position is now the anatomically correct position for this specific cuff and suction anchor assembly for this specific heart. Now the assembled cuff and suction anchor assembly can be pushed into position underneath the heart so that the apex of the heart is positioned within apex cup 48 of suction anchor 40 for a proper and easy orientation of the assembled cuff and suction anchor with respect to the heart with minimal displacement of the heart. The cuff can then be closed in position by looping the cuff 10 about the heart and connecting fastener 16, and, if desired, belts 64, 66 can be placed about the now-closed cuff 10. The remaining operation of the cuff of FIG. 12 is identical to that described above for FIGS. 1 and 8 and, therefore, a further description thereof has been omitted for the sake of brevity.

Figure 14:
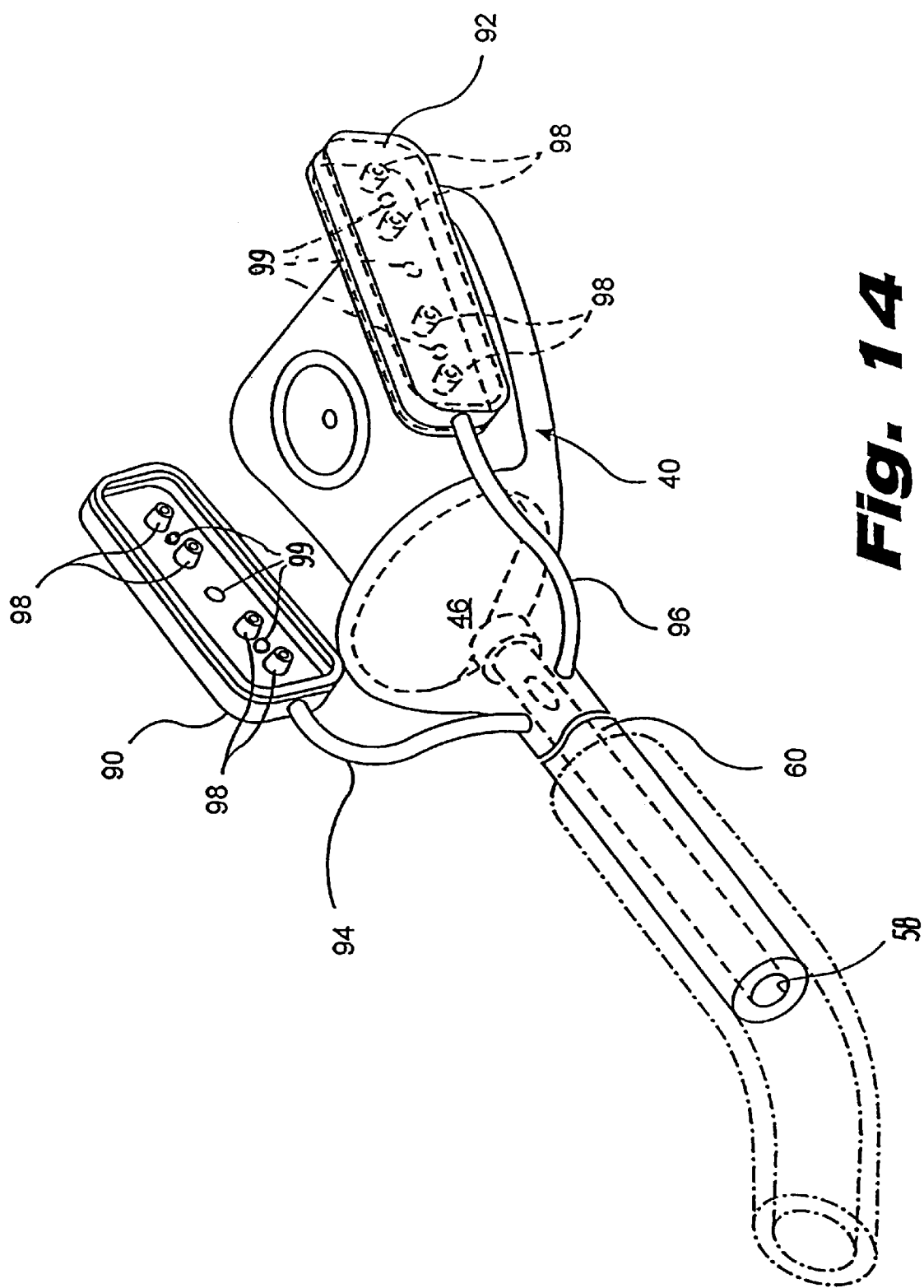
FIG. 14 is a perspective view of one illustrative embodiment of a suction anchor having a pair of suction pads connected thereto.
Figure 15:
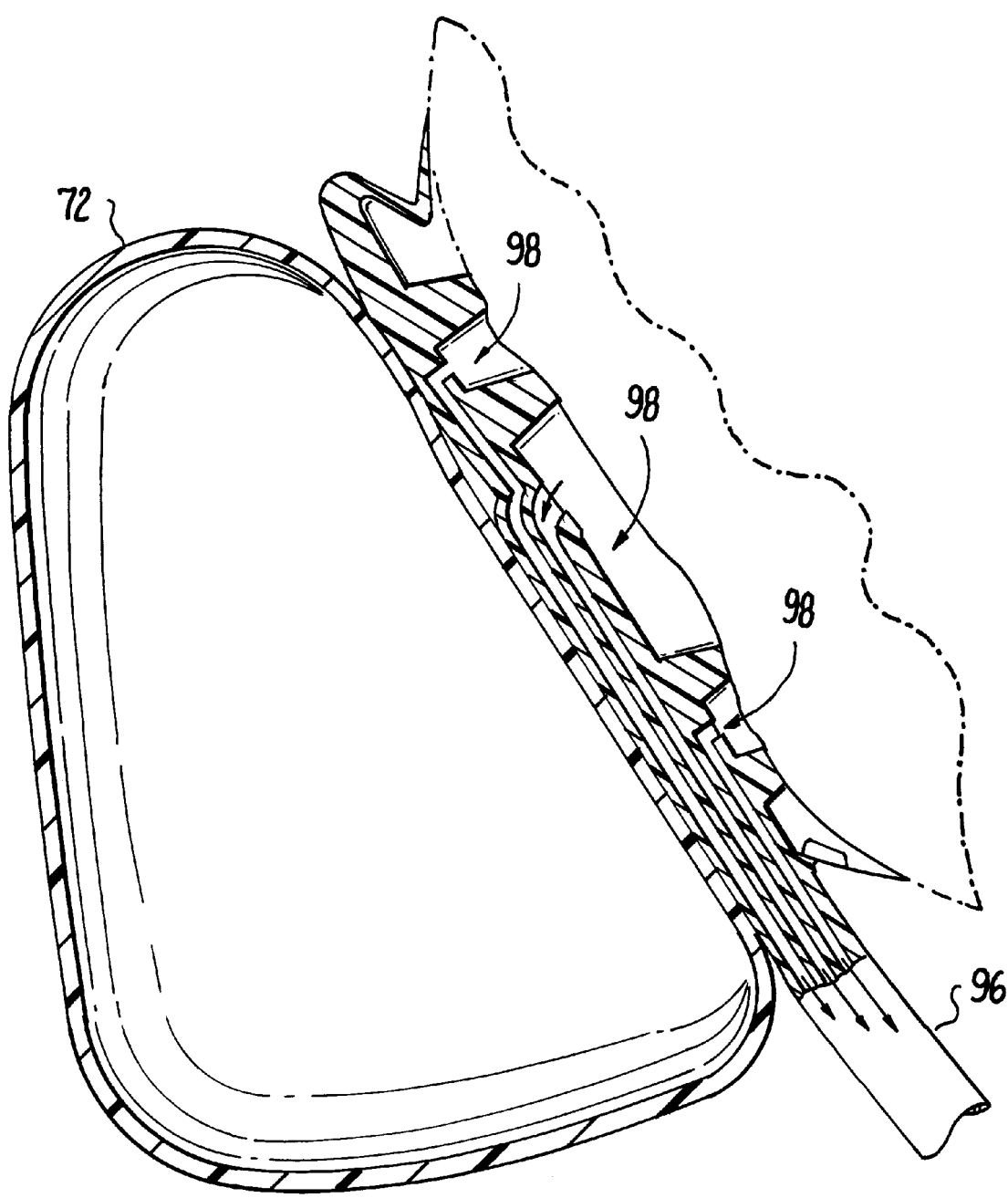
FIG. 15 is a partial cross-sectional view of the suction anchor illustrated in FIG. 14 disposed between an inflatable bladder and a heart.

Referring now to FIGS. 14 and 15, a further embodiment of the ventricular cuff 10 is illustrated. In this embodiment, the suction anchor 40 includes a pair of suction pads 90, 92 that are tethered via respective vacuum lines 94 and 96 to the handle portion 60 of suction anchor 40. Placement depends on the specific heart, so tether lines allow for flexibility. Pads 90 and 92 each preferably include plural cleats 98 between which are interposed respective openings 99 that are in fluid in communication with suction conduit 58. Suction pads 90, 92 and tether vacuum lines 94, 96 are preferably made of a sufficiently pliable material such that pads 90, 92 may be maneuvered into position between bladder 14 and the heart when the device is in use. Thus, the pressure applied to the ventricles of the heart by bladder 14 should not be substantially affected due to the placement of pads 90, 92. However, pads 90, 92 assist in maintaining the position of the heart within the ventricular cuff 10 by preventing movement of the heart with respect to the suction anchor 40.

Referring now to FIG. 16, an exemplary suction cup 100 is illustrated. The suction cup 100 can be used as a suction pad in the suction anchor 40, or as the suction cup in suction pads 90, 92. The suction cup 100 includes a sealing lip 102 that seals with respect to the surface of the heart. The suction vacuum pressure is applied through a conduit 104 at approximately the center of suction cup 100. A plurality of upwardly projecting cleats 106 are positioned throughout a lower surface wall 108 of suction cup 100. The upwardly projecting cleats 106 prevent movement of the heart in a shearing direction (i.e., substantially perpendicular to the direction of suction force), thereby minimizing trauma to the heart tissue and allowing adequate area for suction force to be applied to the heart. In addition a bar 110, which also functions as a cleat, is disposed over conduit 104 to prevent heart tissue from entering conduit 104, thereby assuring a uniform distribution of the vacuum holding force within suction cup 100 about sealing lip 102. Sealing lip 102 has a flexible bellow wall 103 to permit lip 102 to form an effective seal with the heart wall even with relative movement between cup 100 and the heart. This relative movement is absorbed by bellow 103.

Figure 17:
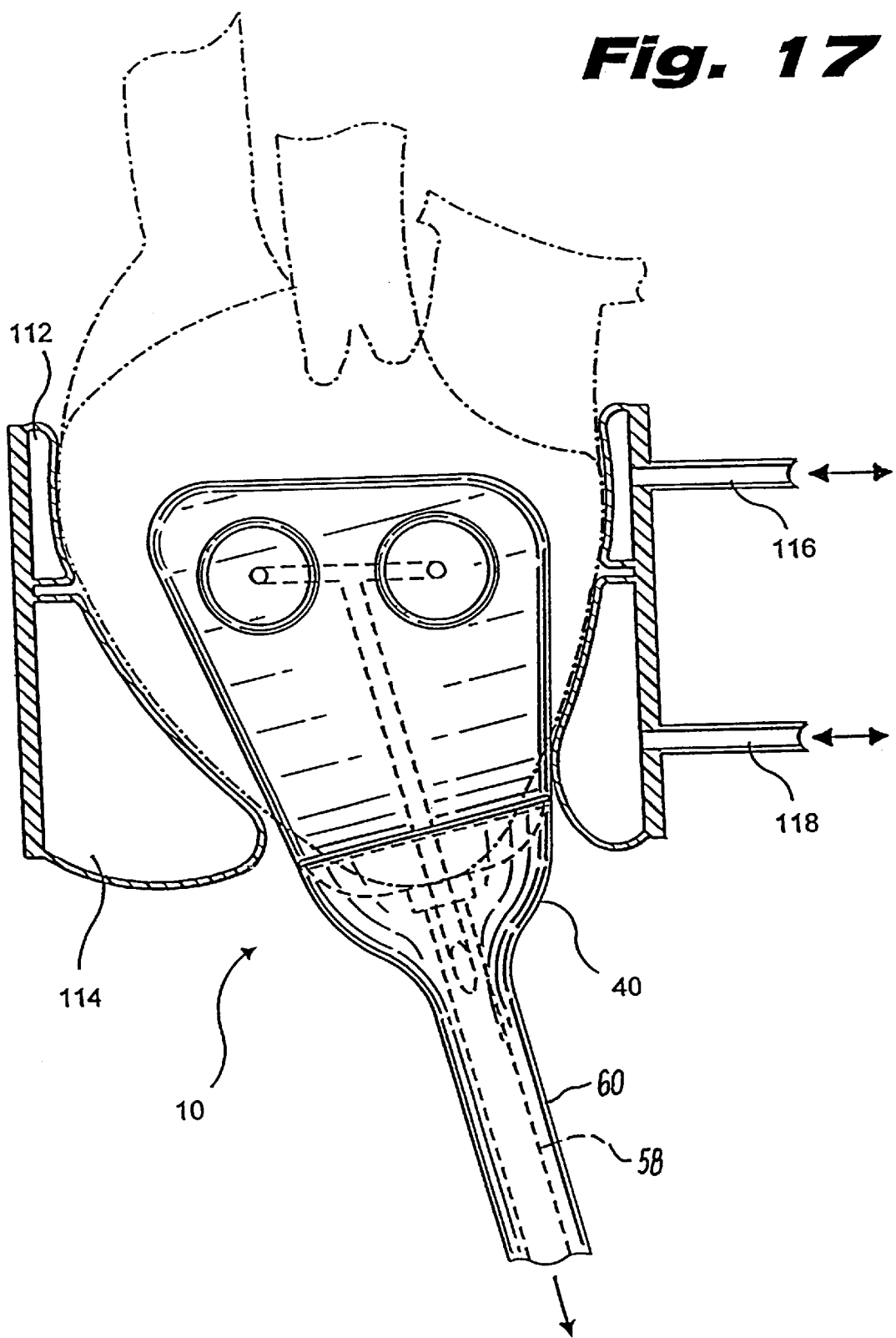
FIG. 17 is a sectional view of an alternate embodiment of the ventricular cuff of the present invention.

Referring now to FIG. 17, an alternate embodiment of the ventricular cuff 10 is illustrated. This embodiment includes two separately inflatable annular bladders 112, 114. Because the outer shape of the heart tapers down from the juncture with the valve plane to the apex, the present inventors have found it advantageous to divide the bladder into two sections to apply more uniform pressure to the ventricles. The lower bladder 114 (i.e., the bladder closer to the apex of the heart), has a relatively wider wall so that it can extend further from outer shell 12 so that it may easily contact the outer surface of the smaller diameter portion of the heart and conform to the outer shape thereof. Each bladder is connected to an inflation conduit 116, 118, respectively to provide for cyclic inflation and deflation of the respective bladders. A suction holding force can be applied to the heart by a suction anchor 40, which is schematically illustrated in FIG. 16.

Figure 18:
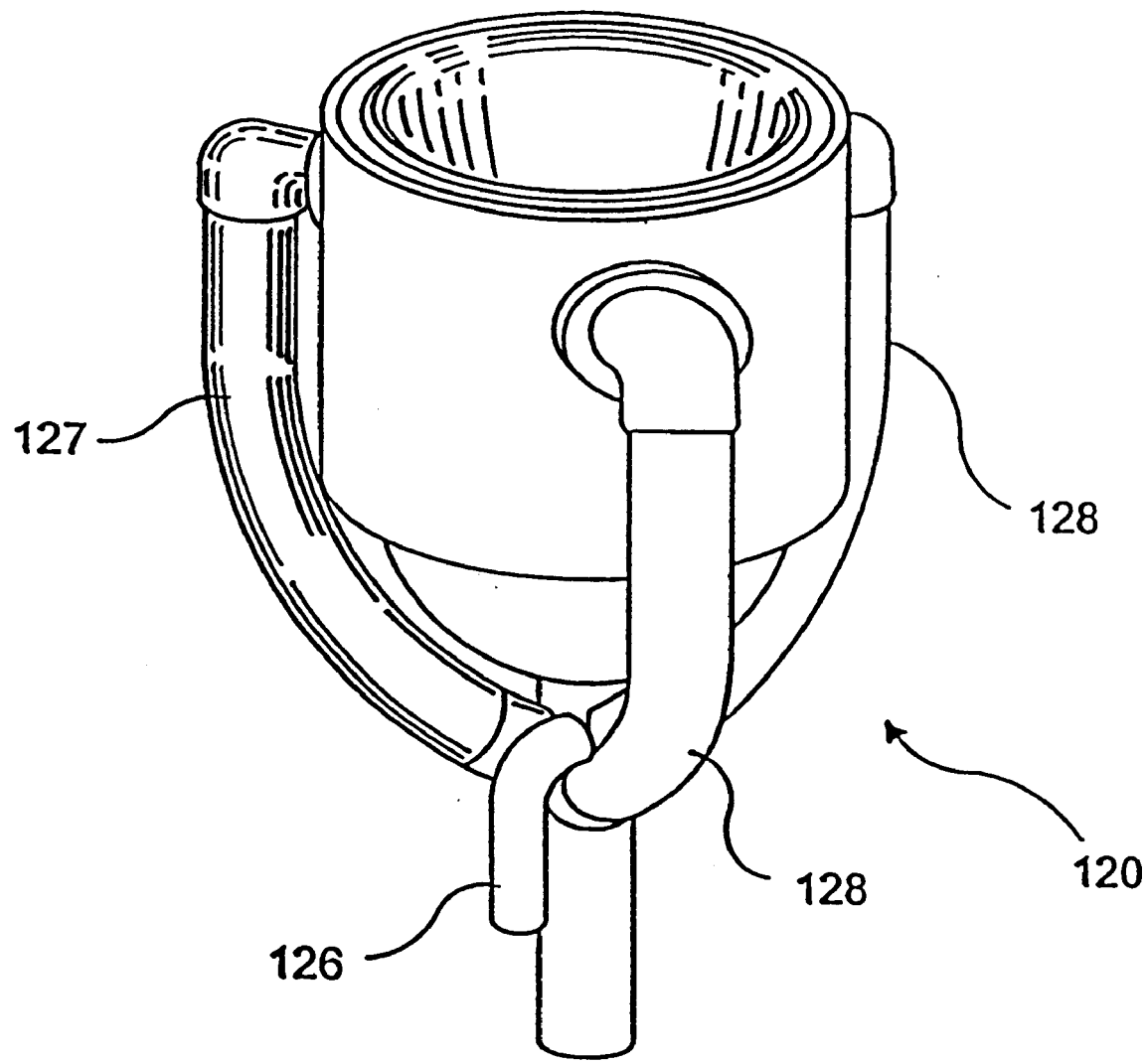
FIG. 18 is a perspective view of yet another illustrative embodiment of the ventricular cuff of the present invention.
Figure 19:
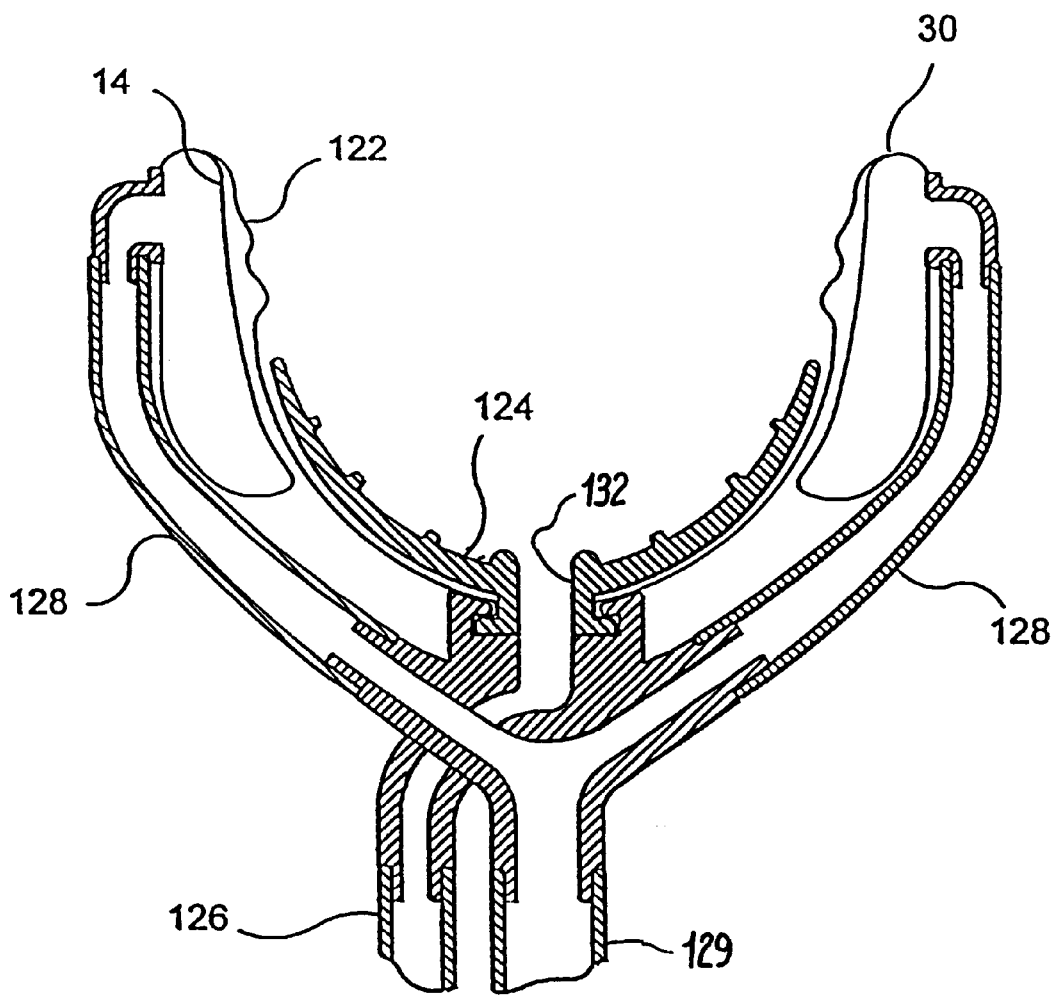
FIG. 19 is a sectional view of the ventricular cuff shown in FIG. 18.
Figure 20:
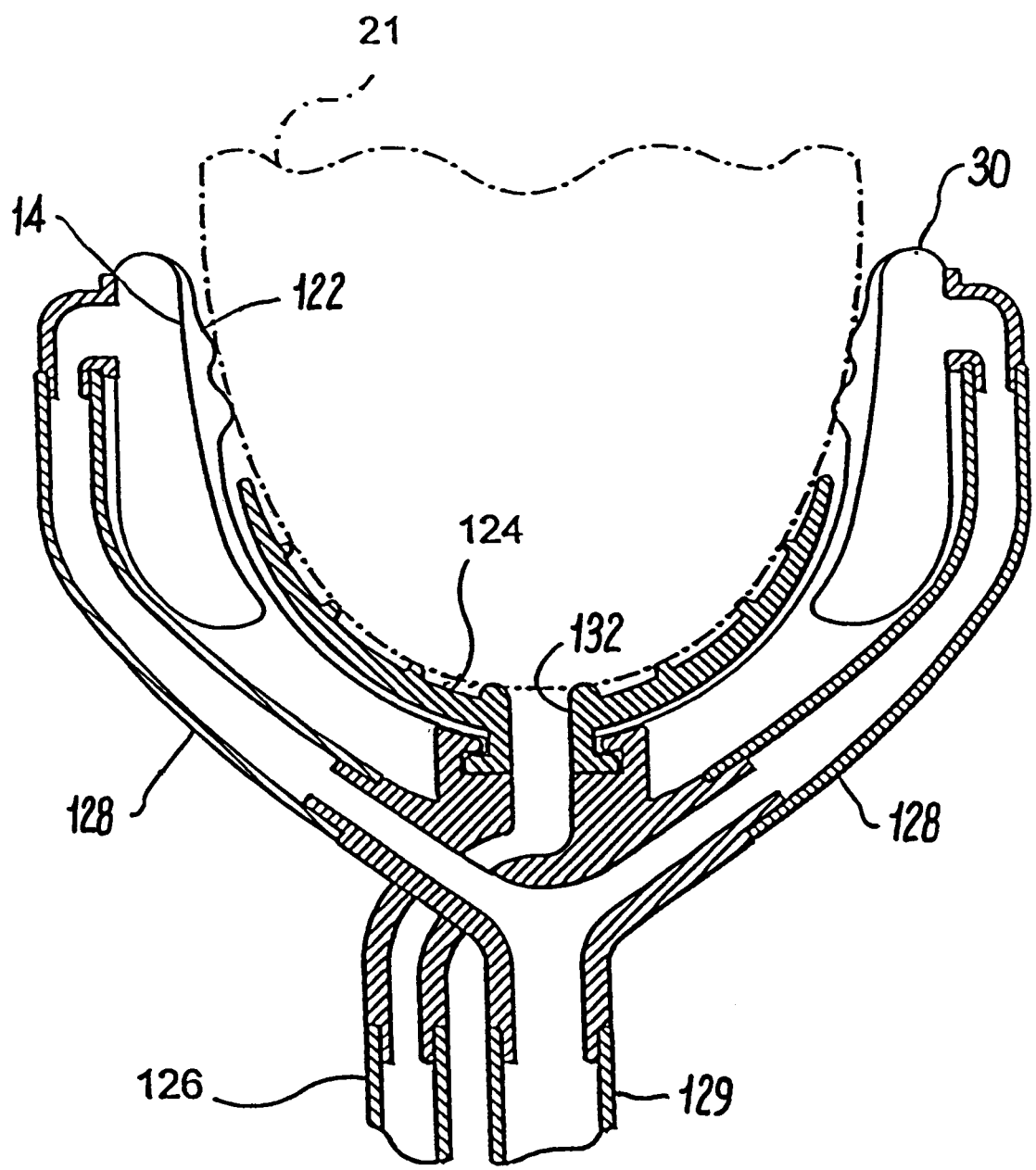
FIG. 20 is a sectional view of the ventricular cuff shown in FIG. 18 with a heart placed within the cuff, with the heart shown in phantom.

Referring now to FIGS. 18–20, an alternate embodiment of a ventricular heart assist device 120 is illustrated. Device 120 includes a suction membrane (bladder) 122 that is disposed radially inwardly of the bladder 14 to be interposed between the bladder and the patient's heart. Additionally, a suction anchor 124 is disposed inwardly of membrane 122 for placement about the apex of the heart. Suction anchor 124 is connected for fluid communication with a suction conduit 126 in a similar manner to suction anchor 40, as described above. In the alternate embodiment, plural inflation/deflation conduits 128 are in fluid communication with the bladder 14 at spaced apart locations, and communicate with a common fluid line 129. Conduits 128 are made of a sufficiently rigid material to support bladder 14 in place relative to the membrane and suction anchor, as is illustrated in FIGS. 19 and 20. The membrane 122 is preferably connected to bladder 14 adjacent the upper end 30 of the bladder, preferably by bonding, heat sealing, RF sealing, laser welding, or any other well known method. The bladder 14 is made of a sufficiently pliable material so that it completely conforms to the shape of the heart and creates no transmural pressure within the bladder. Thus, substantially the entire pressure exerted by bladder 14 is transmitted directly to the external ventricular surface of heart 21 (FIG. 20).

Figure 21:
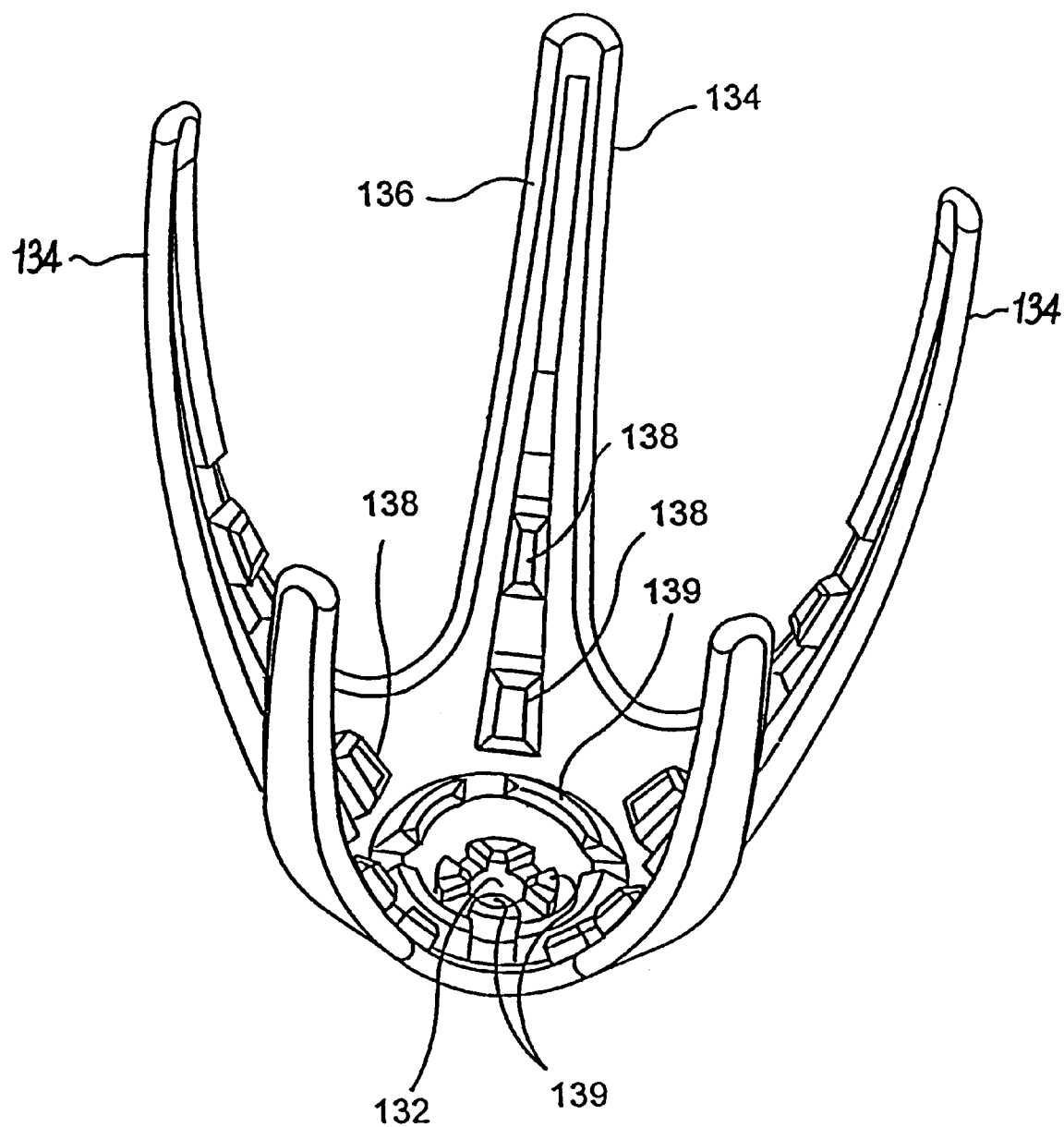
FIG. 21 is a perspective view of an alternate embodiment of a suction anchor included in the ventricular cuff of FIG. 20.

Referring now to FIG. 21, the suction anchor 124 is illustrated in more detail and includes a central opening 132 that is in fluid communication with suction conduit 126. Suction anchor 124 includes a plurality of upwardly projecting fingers 134, for example five such fingers. The fingers are inwardly concave and each includes an outer perimeter sealing lip 136 to permit suction anchor 124 to seal with respect to the lower portion of the heart adjacent the apex. A plurality of projecting cleats 138 are disposed inside of lip 136 to help support the heart and prevent a shearing movement between the heart and suction anchor 124. Plural cleats 139 are disposed in the base of the suction anchor for placement against the apex of the heart.

Figure 22:
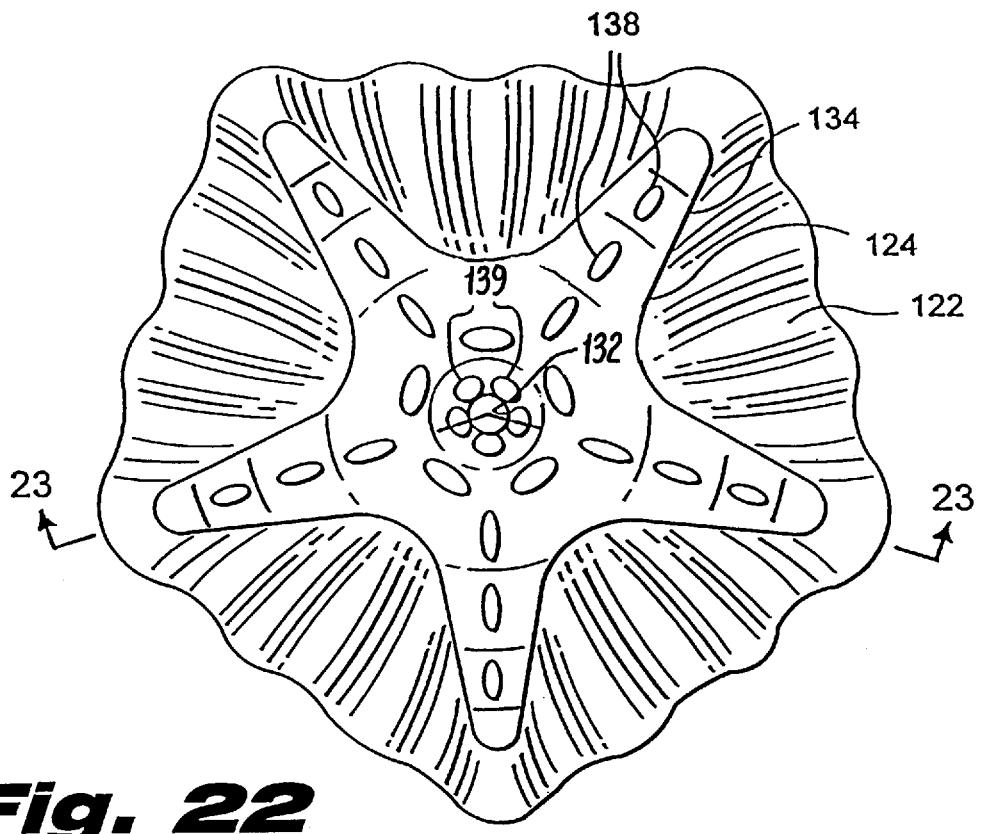
FIG. 22 is a partial top plan view of the suction anchor and membrane illustrated in FIG. 20.
Figure 23:
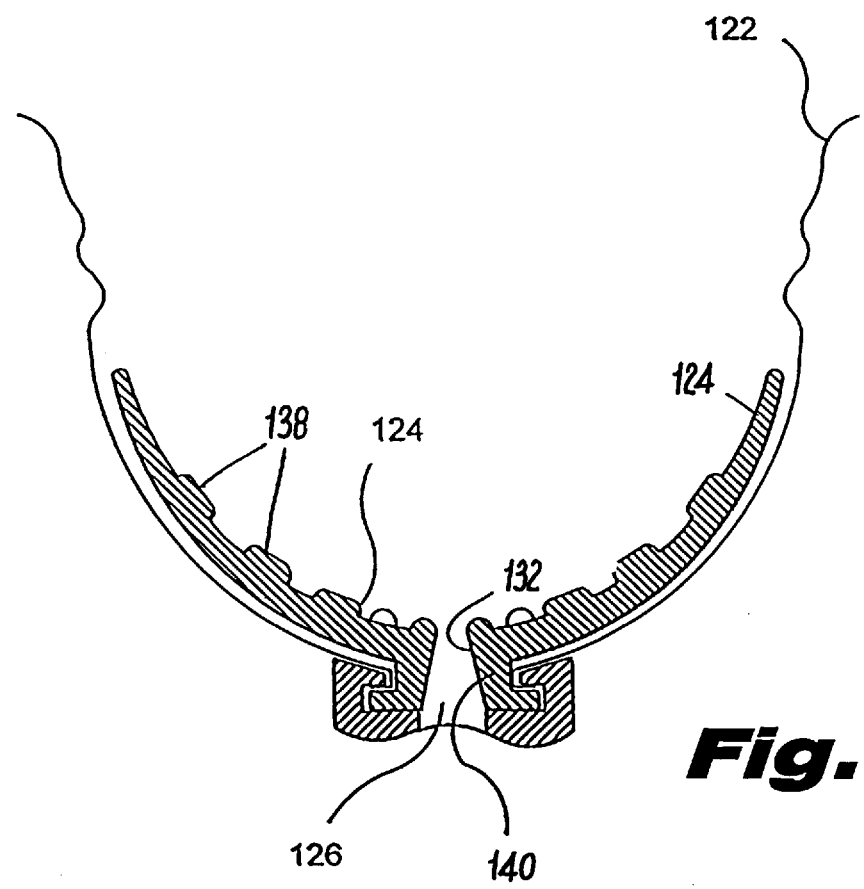
FIG. 23 is a partial sectional view of the suction anchor and membrane illustrated in FIG. 22.

Referring now to FIGS. 22 and 23, a partial top view and a partial sectional view of the suction anchor 124 and membrane 122 is illustrated. Cleats 138 and 139 prevent the outer surface of the heart from being drawn into the suction line 126. The cleats serve to distribute the force over the area of the heart engaged by the respective fingers by preventing sealing of the opening 132. Cleats 138, 139 also create air paths to maximize the suction area and, thereby, help prevent slippage of the heart with respect to suction anchor 124. Collapsible suction membrane (bladder) 122 additionally serves as a large suction bag. The lower portion of the bag (i.e., that portion of the bag closest to the apex of the heart) is attached to a base 140 of the fingers 124 about suction conduit 126. Both membrane 122 and fingers 124 are made of a sufficiently pliable material so that they conform to the outer surface of the heart.

Figure 24:
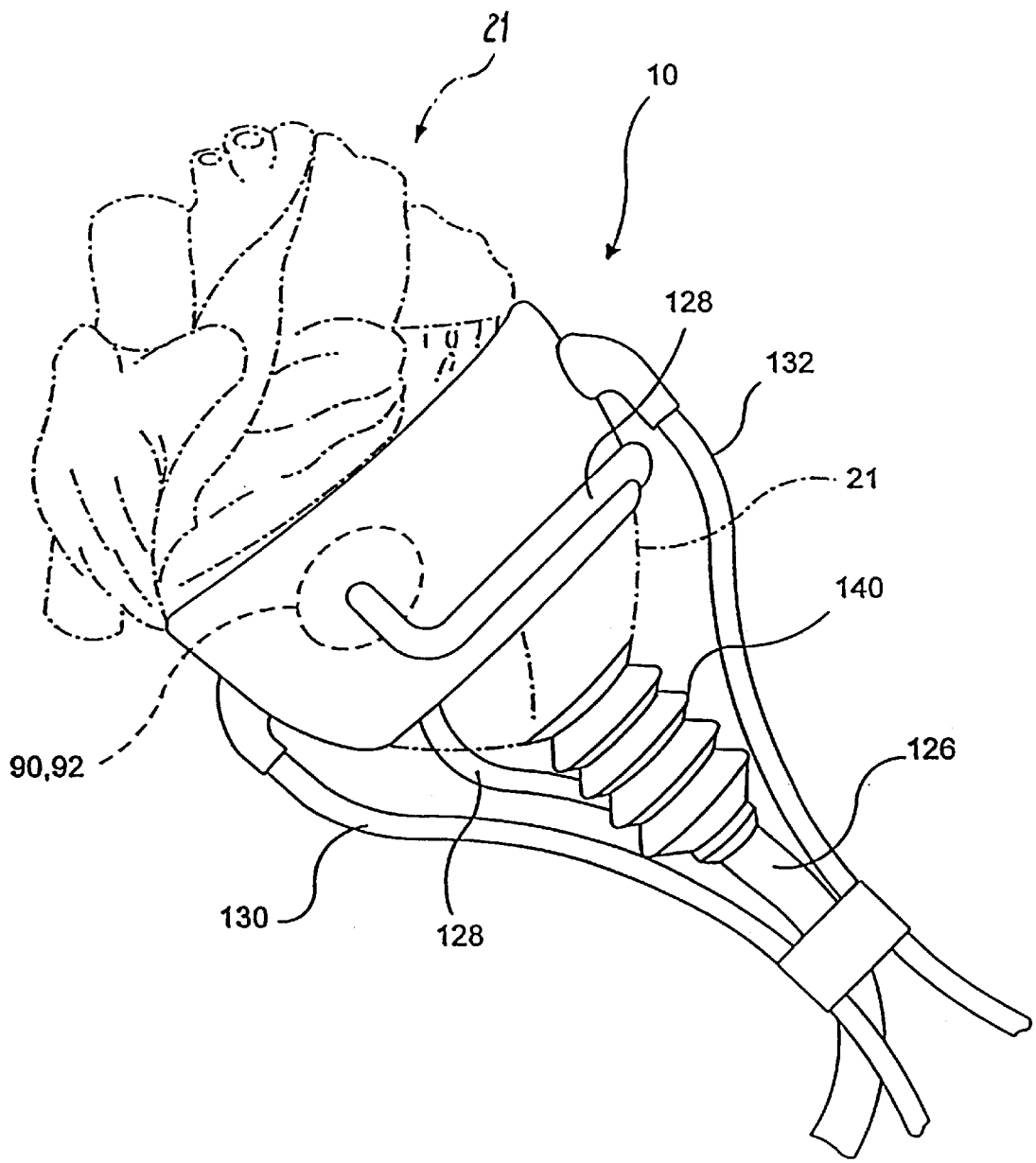
FIG. 24 is a perspective view of an alternate embodiment of a ventricular cuff according to the present invention.

Referring now to FIG. 24, another embodiment of the ventricular cuff is illustrated. In this embodiment, suction pads 90 and 92 are illustrated being connected to the suction line 128, which is connected for fluid communication with the conduit 126. Additionally, suction bellows 140 is positioned against the apex of the heart. The use of bellows 140 permits relative movement to take place between suction conduit 126 and heart 21 to ensure that cuff 10 is not displaced from the heart 21. Thus, suction conduit 126 can be fixedly mounted to the chest wall during use without risk of movement of the heart. Conduits 130, 132 are inflation ports and are in fluid communication with bladder 14.

Figure 25:
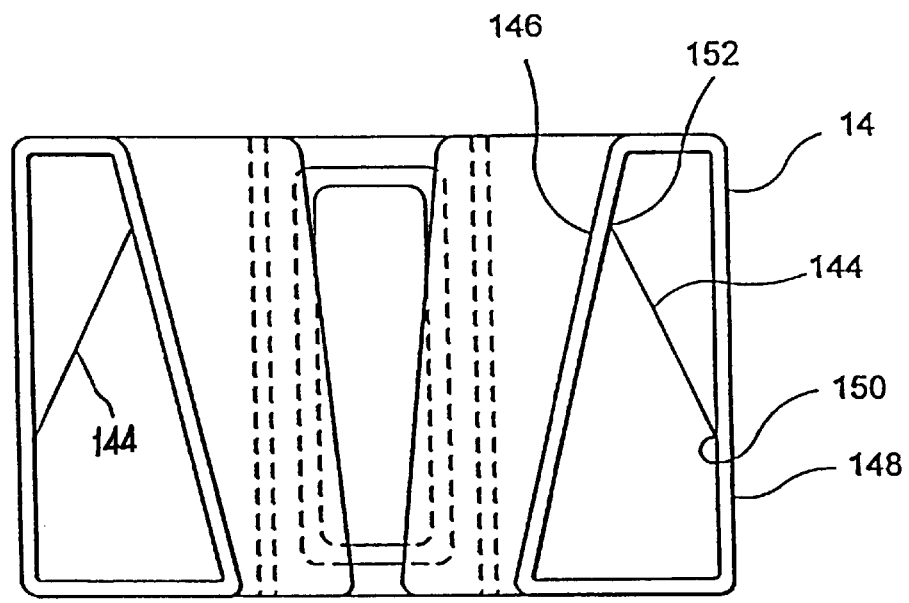
FIG. 25 is a sectional view of an alternate embodiment of an inflatable bladder included in the ventricular cuff of the present invention.
Figure 26:
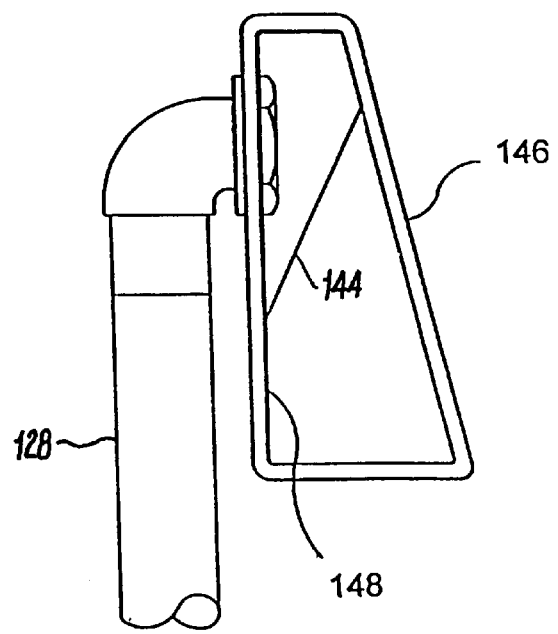
FIG. 26 is a partial sectional view of the bladder illustrated in FIG. 25.
Figure 28:
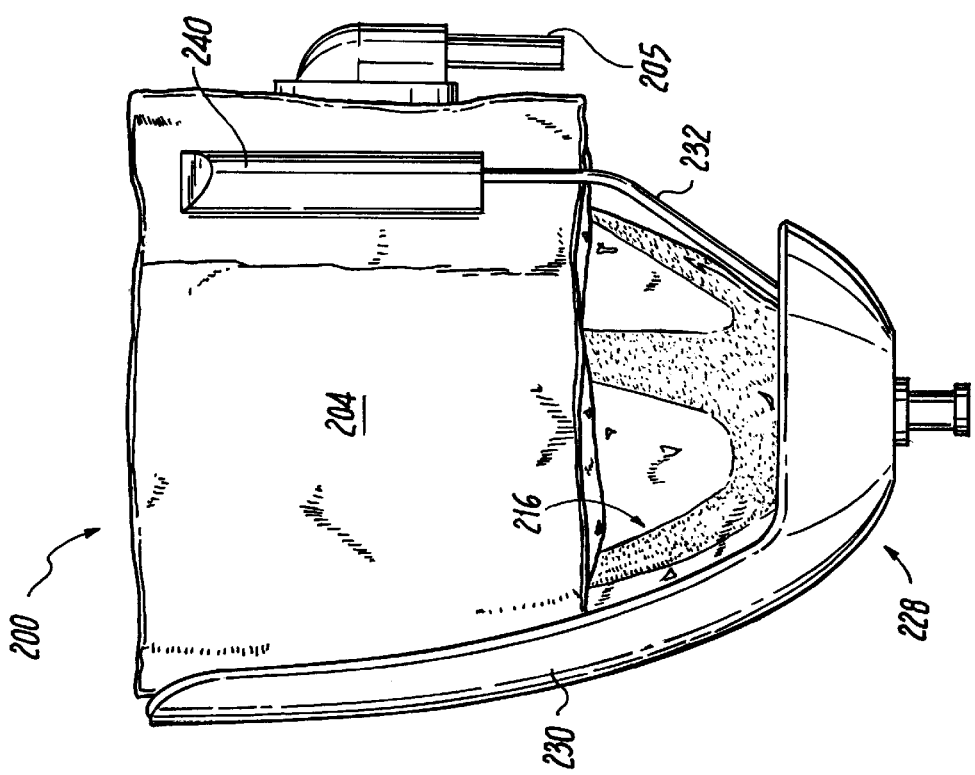
FIG. 28 is a side view of the ventricular cuff of FIG. 27.

Referring now to FIG. 25, the bladder 14 is illustrated having a plurality of cords 144 that are connected from an internal wall 146 to an external wall 148 of the bladder. As discussed above, the external wall of the bladder is the internal wall of outer shell 12. Cords 144 are utilized to limit the amount of relative movement of the internal wall 146 of bladder 14. The first end of cord 144 is fixedly attached to the external wall 148 at position 150 and the opposite end of the cord 144 is connected to internal wall 146 at position 152. Cords 144 are preferably made from an inelastic material and, therefore, limit the amount of upward movement of the inner wall 146 of the bladder 14 away from the apex region of the bladder. Of course, cords 144 could also be made of an elastic material, but this is less preferred. Cords 144 prevent the inner wall 146 of bladder 14 from bulging out of the cuff, thereby impinging on the atrial region of the heart. Thus, it is preferable to limit the upward movement of membrane 14 so that, during the diastolic phase, the inner wall 146 will not be caught outside of the cuff.

Figure 27:
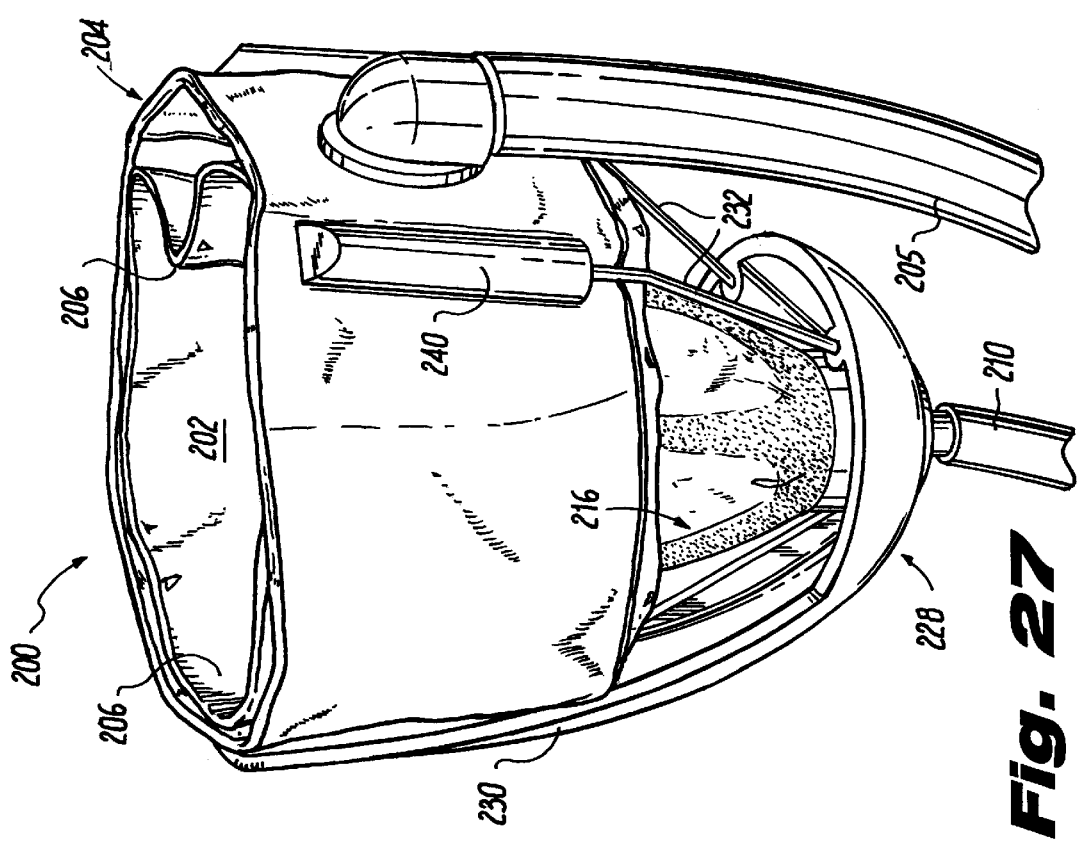
FIG. 27 is partially fragment perspective view of another illustrative embodiment of a ventricular cuff of the present invention.

Referring now primarily to FIG. 27, there is shown another preferred embodiment of the ventricular cuff 200 of the present invention. In this alternative embodiment, the cuff is in the form of an upwardly opening receptacle defining an interior chamber 202 sized for making a relatively close fit about at least a portion of a patient's heart. The chamber is defined by an annular inflatable bladder 204 and an upwardly opening suction membrane 206 disposed inwardly of the bladder. The suction membrane includes a central opening 208 formed in the lower end thereof that is engaged to one end of a vacuum tube 210 for fluid communication therebetween. The other end of the vacuum tube is connected to a vacuum source (not shown) that is operative to draw air through the vacuum tube. The suction membrane is preferably formed of a thin polyurethane membrane and is biocompatible and Gamma Sterilization compatible. The suction membrane is preferably connected at its upper end to the upper end of the bladder by means of UV adhesive, cyanoacrylate, heat sealing, or other suitable means. Thus, the cuff may be extended over the ventricles of the heart, the vacuum tube connected to the vacuum source, and the vacuum source actuated to withdraw air from the chamber 202 to create a partial vacuum within the chamber, which causes the suction membrane to be drawn radially inwardly and into secure engagement with the heart.

The bladder 204 is preferably made from biocompatible, reinforced polyurethane, or any other suitable elastic polymer. The polyurethane defines a fluid impermeable layer that is reinforced with a non-stretchable reinforcing layer, for example a polyester weave. The outer wall 207 of the bladder is preferably thicker than the inner wall 209 thereof to resist radial outward expansion of the bladder. The outer wall is further formed with one or more openings 212 that are in fluid communication with first ends of respective flexible fluid lines 214. Preferably, elbow fittings are attached to the bladder wall via snap fit connectors (not shown), the elbow fittings including inlet ports sized for engaging the first ends of the fluid lines and outlet ports opening into the interior of the bladder for fluid communication therebetween. The respective second ends of the fluid lines are connected to one or more sources of pressurized fluid (not shown). Thus, actuation of the source or sources of pressurized fluid causes the bladder to be inflated, with the inner wall being driven radially inwardly to exert a force against the surface of the ventricles to assist the ventricles in pumping blood, as is described above.

Figure 29:
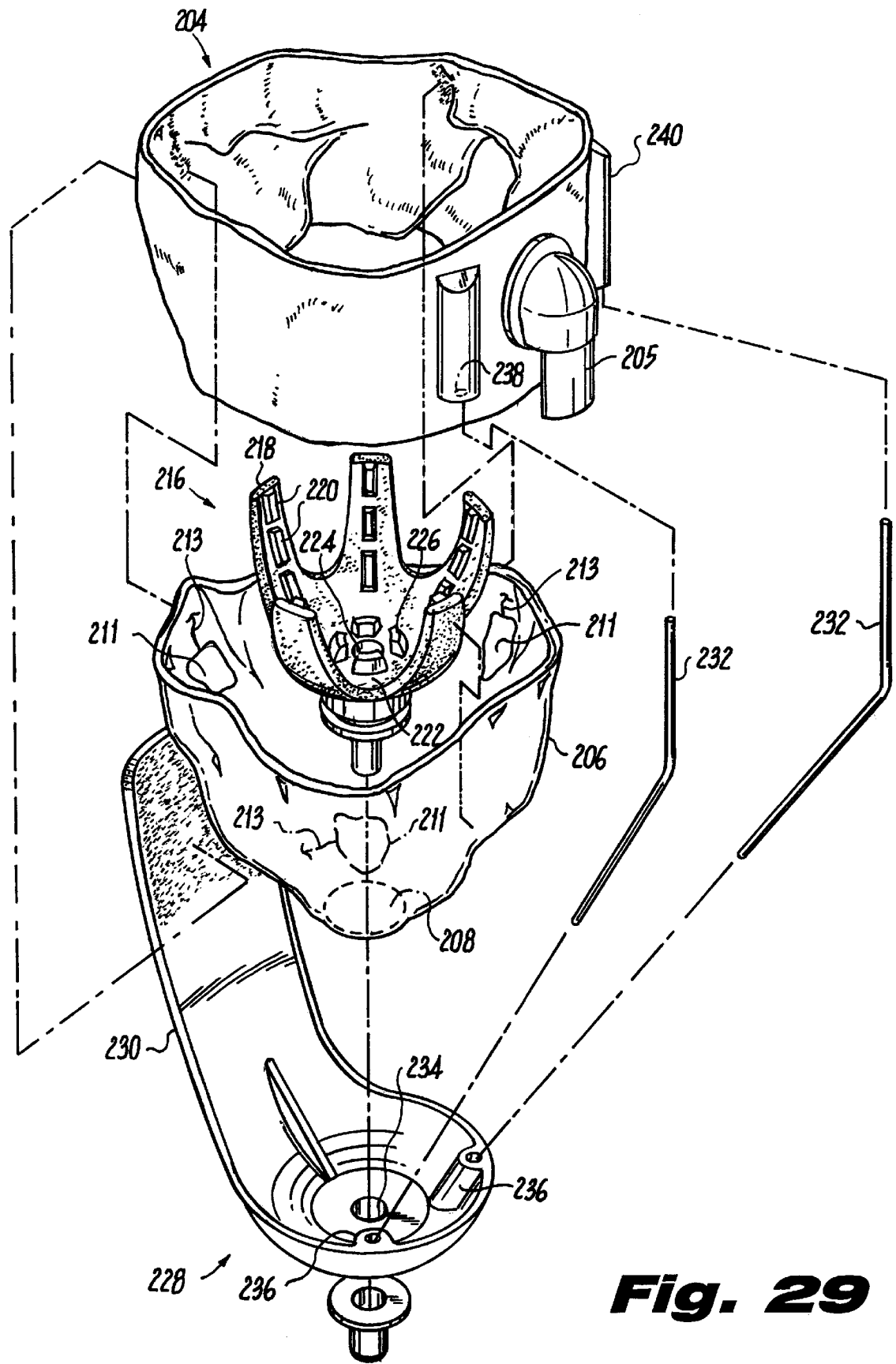
FIG. 29 is an exploded perspective view of the ventricular cuff of FIG. 27.

In a preferred embodiment, when the bladder is deflated the inner wall of the bladder folds in upon itself while remaining in relatively close proximity to the heart (FIG. 29). Then, as the bladder is inflated, the inner wall at least partially unfolds as it is driven radially inwardly to uniformly engage the portion of the heart that is contained within the cuff 200. In this manner, the bladder need not stretch in order to engage the heart, resulting in a substantially uniform application of force to the ventricle outer walls, without any significant loss due to transmural pressure in the inner wall of the bladder because the bladder is not stretched as it is inflated. In addition, because the bladder does not stretch, the heart is not contorted into an generally hourglass shape when the bladder is inflated and comes into contact with the heart.

As with the other embodiments described above, the cuff 200 is preferably designed such that it extends over the heart to a position just below the atrioventcular (AV) groove.

Figure 30:
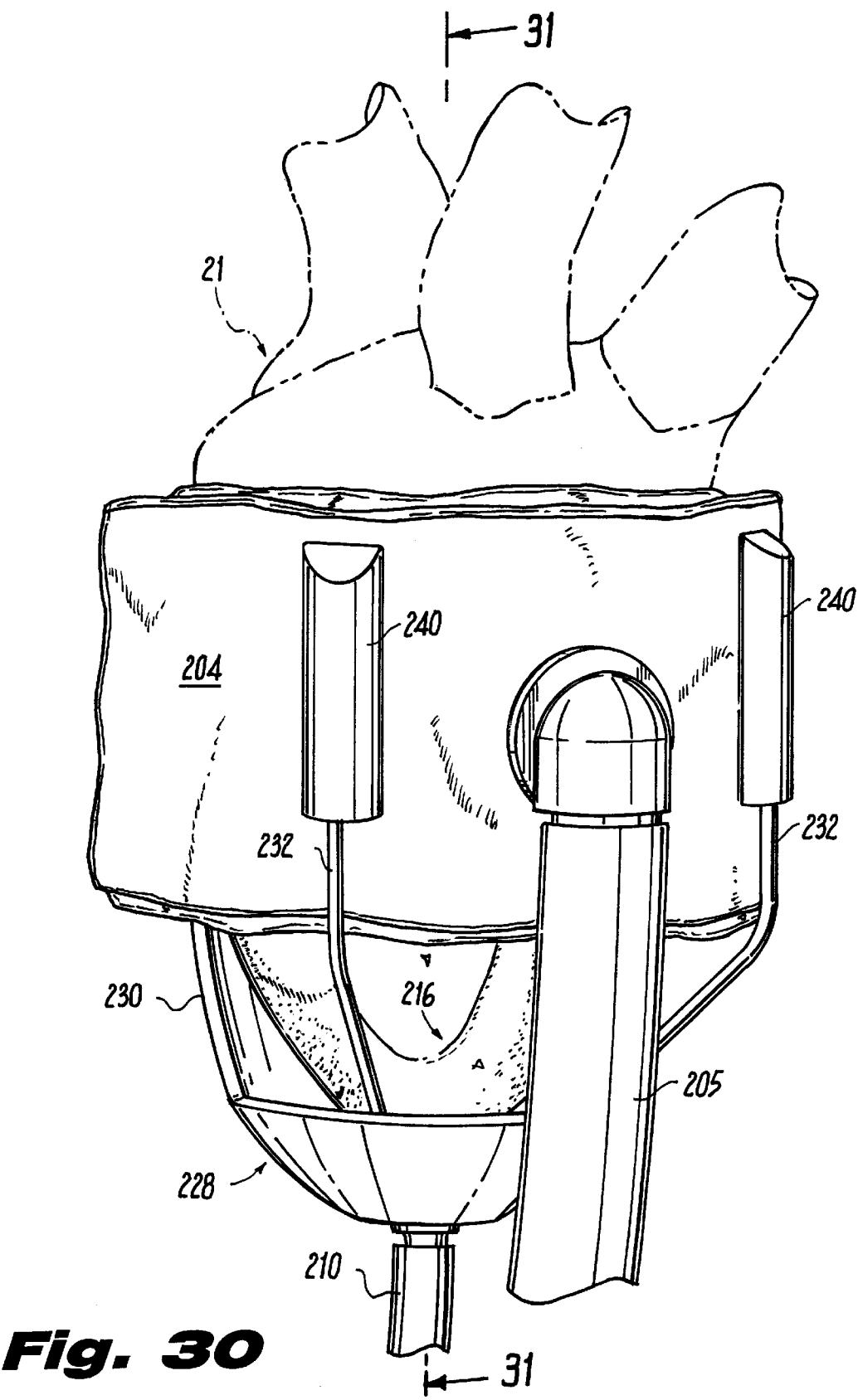
FIG. 30 is a perspective view of the ventricular cuff of FIG. 27 in place about a heart, with the heart being shown in phantom.
Figure 31:
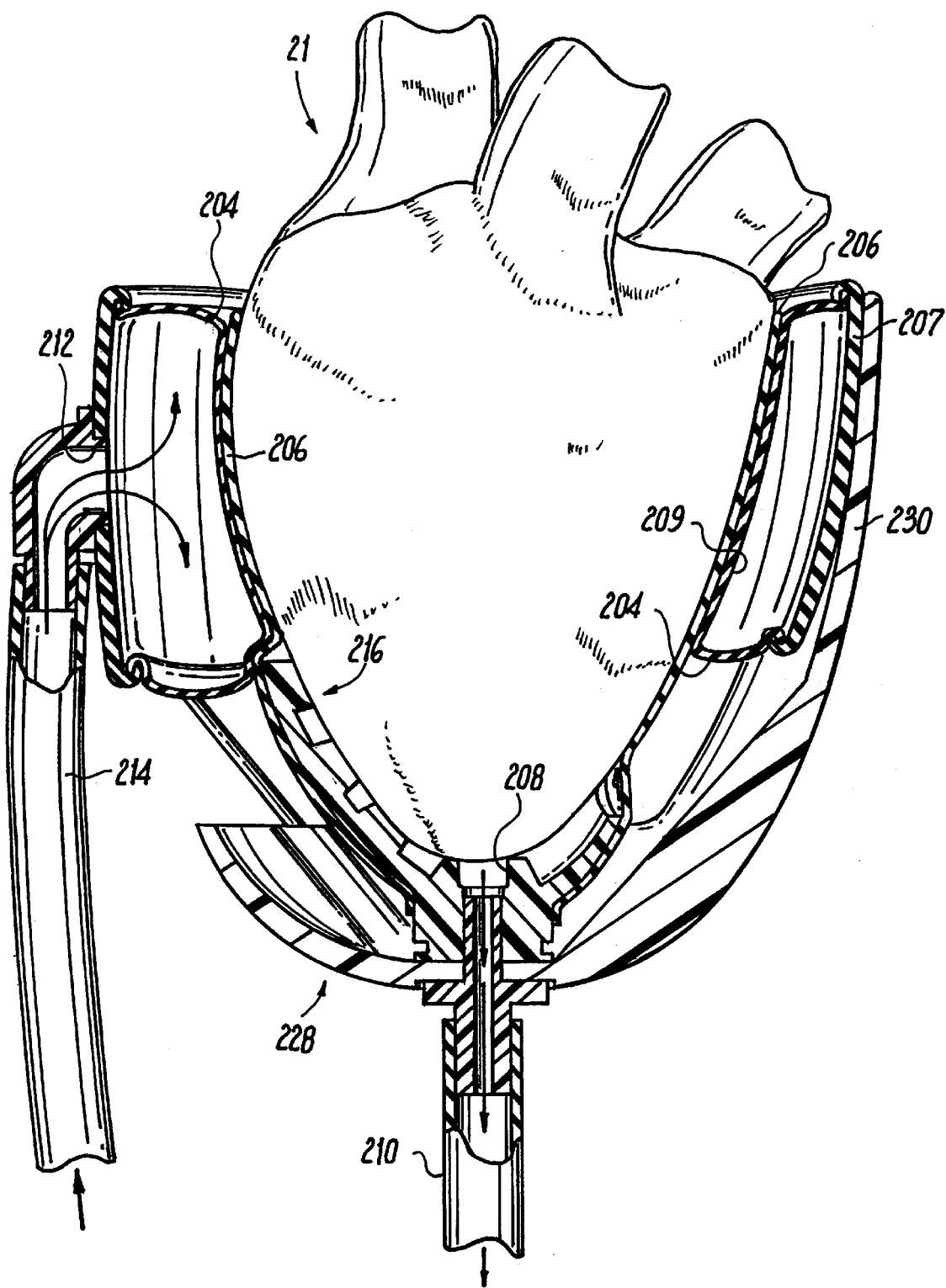
FIG. 31 is a cross-sectional view of the ventricular cuff of FIG. 27.

The ventricular cuff 200 further includes a flexible, cleated finger assembly 216 for releasably engaging the outer surface of the heart (see FIGS. 29–31). The flexible cleated finger assembly is disposed inwardly of the suction membrane 206, such that when the suction membrane is drawn inwardly against the heart, the fingers are driven into contact with the patient's heart. The finger assembly is preferably molded of a very flexible polymer, such as polyurethane, silicone, TPE, etc., and is connected to the inner surface of the suction membrane 206 by means of a UV adhesive, adhesive, heat sealing, or other suitable means. The finger assembly includes plural fingers 218, for example five, each of which includes plural projecting cleats 220 to engage the outer surface of the heart. The finger assembly further includes a base 222 engaged to the suction membrane 206 and formed with a central opening 224 aligned with the opening in the suction membrane for fluid communication therethrough. The base also includes plural raised cleats 226 which surround the opening 224 to prevent the heart tissue from plugging the opening when the vacuum source is actuated. The cleats and fingers cooperate to define plural fluid flow paths to allow fluid to be drawn from substantially the entire chamber through the vacuum line 210. In this manner, the holding force is distributed over a large portion of the surface of the heart rather than being concentrated at the apex of the heart, resulting in a more secure engagement of the cuff to the patient's heart without a large force being applied to a small area of the heart.

The ventricular cuff 200 further includes an apical reinforcing support assembly including a spatula 228, a backplate reinforcement 230, and a pair of supporting rods 232. The spatula is preferably formed of semi-rigid polymer such as polyurethane, nylon, TPE, and the like, which is securely engaged to the bottom ends of both the finger assembly 216 and the suction membrane 206. The spatula thus serves to hold the finger assembly and suction membrane in place relative to the bladder 204. The spatula is formed with a central opening 234 for extension therethrough of the vacuum line 210.

The backplate reinforcement 230 is preferably formed integral with the spatula 228 and is also preferably formed of semi-rigid polymer, such as polyurethane, nylon, TPE, and the like. The backplate reinforcement is connected to the outer wall of the bladder 204 by means of a layer of adhesive, by heat sealing, or the like. The backplate is designed for alignment with the inferior portion of the heart, and thus the portion of the bladder aligned with the backplate is preferably not inflatable.

The supporting rods or stylettes 232 are in the form of curved segments of a non-flexible metal such as titanium or the like. The respective bottom ends of the rods are received in respective upwardly opening receptacles 236 formed in the spatula 228. The rods angle upwardly and outwardly from the spatula, and then turn to extend upwardly and terminate in respective upper ends that are received in receptacles 238 formed in respective stylette caps 240 that are bonded to the outer wall of the bladder 204 by means of an adhesive or other suitable means well known to those skilled in the art. The receptacles are preferably formed of a flexible polymer, such as polyurethane, nylon, TPE, and the like. The rods are preferably spaced approximately 90°–120° apart. The rods provide support for the bladder as the bladder and suction membrane 206 are extended over the heart, and cooperate with the backplate reinforcement to facilitate extension of the bladder and suction membrane over the heart.

Referring now to FIG. 29, in one illustrative embodiment, a plurality of sensing electrodes 211 are mounted on the internal surface of suction membrane 206. Electrodes 211 are used to detect the myocardial ECG signals generated by the heart and to generate a corresponding electrical signal. It will be apparent that the electrodes could alternatively be placed at some other suitable location on the cuff 200, so long as they are in sufficiently close proximity to the heart to sense the heart's electrical activity. Each of the electrodes is connected to a corresponding electrical lead 213 which conducts the respective electrical sense signals. The electrodes may comprise components of, for example, an apparatus for detecting R-waves from a patient's heart, which is operative to sense the heart's electrical activity, detect the rising edge of an R-wave, and generate a synchronous pulse signal in response thereto. Such a system is disclosed in commonly owned U.S. Provisional patent application Serial No. 60/093,918 entitled "Digital ECG Detection System", filed on Jul. 23, 1998, the disclosure which is hereby fully incorporated by reference. Briefly, the apparatus comprises the electrodes 211 configured to be placed in close proximity to the heart and which sense the electrical activity of the heart and generate corresponding electrical signals conducted via the respective leads 213. The apparatus also includes a signal processor (not shown) in communication with the respective electrodes 211 via the leads 213 to receive the electrical signals. The signal processor is programmed to condition the incoming electrical sense signals, to calculate a variable threshold value, and to determine whether the magnitude of the conditioned electrical signal exceeds the threshold value and, if so, to generate a corresponding pulse signal, to signify the detection of a rising R-wave.

The use of the embodiment disclosed in FIGS. 27–31 is similar to that of the other embodiments described above. The cuff 200 is extended over the patient's heart, with the apex of the heart disposed within the interior chamber 202 adjacent the lower end thereof. The vacuum line 210 is then connected to the vacuum source and the vacuum source is actuated. The fluid (gas or liquid) within the chamber is drawn through the vacuum line, thereby creating a partial vacuum within the chamber, which draws the suction membrane 206 and finger assembly 216 inwardly and into contact with the patient's heart. The inlet line 205 is then connected to a source of pressurized fluid, which is actuated to repeatedly inflate and deflate the bladder 204 at a predetermined rate. While it is being inflated, the inner wall of the bladder unfolds and engages substantially all of the surface area of the heart that is contained within the chamber. Continued inflation of the bladder results in the ventricles being compressed over substantially the entire length thereof to improve the pumping capability of the heart.

From the foregoing, it will be apparent that the ventricular cuff of the present invention provides an efficient, reliable device for assisting a malfunctioning heart to pump blood by applying a substantially uniform, intermittent pressure to the ventricle outer walls.

While the invention has been particularly shown and described with reference to illustrative embodiments thereof, it will be understood by those skilled in the art that various changes in form and details may be made therein without departing from the spirit and scope of the invention. Accordingly, it is not intended that the invention be limited, except as by the appended claims.

We claim:

1. An apparatus for assisting a heart to pump blood, the apparatus comprising:
    an inflatable bladder configured to extend about at least a portion of the heart, the bladder being selectively inflatable to contract the portion of the heart, the bladder being formed of substantially inelastic material;
    a suction membrane configured to make a close fit over at least a portion of the heart, the suction membrane defining an interior chamber to receive at least the portion of the heart therein;
    a suction line in communication with the interior chamber of the suction membrane, the suction line being operative to withdraw fluid from the chamber, thereby drawing the suction membrane inwardly and into engagement with the heart; and
    an inlet line connected for communication with the bladder, the inlet line being operative to selectively deliver pressurized fluid to and withdraw pressurized fluid from the bladder to alternately inflate and deflate the bladder.

2. The apparatus of claim 1, wherein the bladder and suction membrane are connected together.

3. The apparatus of claim 2, wherein the bladder and suction membrane are connected together adjacent the respective upper ends of the bladder and suction membrane.

4. The apparatus of claim 1 further comprising at least one resilient reinforcing finger disposed inwardly of the suction membrane, the reinforcing finger including plural cleats to releasably engage the heart when the suction line is operative.

5. The apparatus of claim 1 further comprising a semi-rigid backplate connected to a portion of the bladder, the backplate being configured for placement against the inferior side of the heart.

6. The apparatus of claim 1, wherein the bladder includes an outer wall and an inner wall, the outer wall being reinforced to resist radially outward expansion during inflation of the bladder.

7. The apparatus of claim 1, wherein the bladder comprises, in combination, a substantially fluid-impermeable film layer and a substantially inelastic reinforcing layer.

8. The apparatus of claim 5 further comprising a spatula engaged to the suction membrane adjacent a lower end of the membrane, the spatula being formed integral with the backplate.

9. The apparatus of claim 1, wherein the bladder comprises plural inflatable compartments, and further comprising:
    plural inlet lines, at least one of which is in communication with each of the respective compartments.

10. The apparatus of claim 1 further comprising at least two inlet lines, each of which is in fluid communication with the bladder at respective spaced apart locations.

11. The apparatus of claim 1, wherein the bladder is in the form of an elongated strip including first and second ends, the bladder being formed of a flexible material to be wrapped about the heart, the bladder further including a fastener device to secure the bladder in place about the heart.

12. A heart contracting device for use in a system for assisting a heart to pump blood, the system including a source of pressurized fluid and an inlet line connected to the source of pressurized fluid for fluid communication therebetween, the heart contracting device comprising:
    a heart engaging device configured to releasably engage the heart;
    an inflatable bladder including an outer wall and an inner wall, the inner wall being formed of substantially inelastic material, the bladder including an inlet port for releasable connection with the inlet line, the bladder being inflatable to drive the inner wall to a heart contracting position;
    wherein the heart engaging device comprises a suction membrane configured to make a close fit about at least a portion of the heart, the heart engaging device further including a suction line in communication with an interior chamber of the suction membrane, the suction line being operative to create a vacuum in the chamber to draw the suction membrane inwardly into engagement with the heart.

13. The heart contracting device of claim 12 wherein the a heart engaging device is connected to the bladder and configured to releasably engage at least a portion of the heart.

14. The apparatus of claim 13, wherein the bladder and suction membrane are connected together adjacent the respective upper ends of the bladder and suction membrane.

15. The apparatus of claim 13 further comprising at least one resilient reinforcing finger disposed inwardly of the suction membrane, the reinforcing finger including plural cleats to releasably engage the heart.

16. The apparatus of claim 13, wherein the heart engaging device comprises a suction anchor shaped to receive a portion of the heart and including at least one suction port to releasably engage the heart.

17. The apparatus of claim 13, wherein the heart engaging device comprises a suction pad with one or more suction ports.

18. The apparatus of claim 12, wherein the outer wall of the bladder is reinforced to resist radially outward expansion during inflation of the bladder.

19. The apparatus of claim 12, wherein the bladder comprises a substantially fluid impermeable film layer and a substantially inelastic reinforcing layer.

20. The apparatus of claim 12, wherein the bladder comprises plural spaced apart inflatable compartments, and further comprising:

plural inlet lines, at least one of the lines being in communication with each of the respective compartments.

21. The apparatus of claim 12 further comprising at least two inlet lines, each of which is in fluid communication with the bladder at respective spaced apart locations.

22. The apparatus of claim 12, wherein the bladder is in the form of an elongated strip including first and second ends, the bladder being formed of a flexible material to be wrapped about the heart, the bladder further including a fastener device to secure the bladder in place about the heart.

23. An apparatus for assisting a heart to pump blood, the apparatus comprising:

a heart engaging device configured to releasably engage the heart;

a source of pressurized fluid; and a bladder formed of substantially inelastic, flexible material and adapted to be positioned about the periphery of at least a portion of the heart, the bladder being connectable to the source of pressurized fluid and inflatable to a heart compressing position to compress at least a portion of the heart;

wherein the bladder is in the form of an elongated strip including first and second ends, the bladder being formed of a flexible material to be wrapped about the heart, the bladder further including a fastener device to secure the bladder in place about the heart.

24. The apparatus of claim 23, wherein the bladder includes an outer wall and an inner wall, the outer wall being reinforced to resist radially outward expansion during inflation of the bladder.

25. The apparatus of claim 23, wherein the bladder comprises a substantially fluid impermeable film layer and a substantially inelastic reinforcing layer.

26. The apparatus of claim 23, wherein the bladder comprises plural inflatable compartments, and further including:

plural inlet lines, at least one of each being in communication with each of the respective compartments.

27. The apparatus of claim 23 further comprising at least two inlet lines, each of which is in fluid communication with the bladder at respective spaced apart locations.

28. The apparatus of claim 23, wherein the heart engaging device comprises a suction membrane configured to make a close fit about at least a portion of the heart, the heart engaging device further including a suction line in communication with an interior chamber of the suction membrane, the suction line being operative to create a vacuum in the chamber to draw the suction membrane inwardly and into engagement with the heart.

29. The apparatus of claim 23, wherein the heart engaging device comprises a suction anchor shaped to receive a portion of the heart and including at least one suction port operative to releasably engage the heart.

30. The apparatus of claim 23, wherein the heart engaging device comprises a suction pad with one or more suction ports that are operative to releasably engage the heart.

31. An apparatus for assisting a heart to pump blood, the apparatus comprising:

a heart engaging device configured to releasably engage at least a portion of the heart;

a source of pressurized fluid; and a bladder adapted to be positioned about the periphery of at least a portion of the heart, the bladder including an inner wall having a predetermined surface area such that the inner wall is at least partially folded when in a deflated state and at least partially unfolds when in an inflated state, the bladder being connectable to the source of pressurized fluid and inflatable to compress at least a portion of the heart;

wherein the heart engaging device comprises a suction membrane configured to make a close fit about at least a portion of the heart, the heart engaging device further including a suction line in communication with an interior chamber of the suction membrane, the suction line being operative to create a vacuum in the chamber to draw the suction membrane inwardly and into engagement with the heart.

32. The apparatus of claim 31, wherein the bladder includes an outer wall and an inner wall, the outer wall being reinforced to resist radially outward expansion of the bladder during inflation thereof.

33. The apparatus of claim 31, wherein the bladder comprises a substantially fluid impermeable film layer and a substantially inelastic reinforcing layer.

34. The apparatus of claim 31 further comprising at least two inlet lines, each of which is in fluid communication with the bladder at respective spaced apart locations.

35. The apparatus of claim 31, wherein the bladder is in the form of an elongated strip including first and second ends, the bladder being formed of a flexible material to be wrapped about the heart, the bladder further including a fastener device to secure the bladder in place about the heart.

36. The apparatus of claim 31, wherein the heart engaging device comprises a suction membrane configured to make a close fit about at least a portion of the heart, the heart engaging device further including a suction line in communication with an interior chamber of the suction membrane, the suction line being operative to create a vacuum in the chamber to draw the suction membrane inwardly and into engagement with the heart.

37. The apparatus of claim 31, wherein the heart engaging device comprises a suction anchor shaped to receive a portion of the heart and including at least one suction port operative to releasably engage the heart.

38. The apparatus of claim 31, wherein the heart engaging device comprises a suction pad with one or more suction ports that are operative to releasably engage the heart.

39. A heart contracting device for use in a system for assisting a heart to pump blood, the system including a source of pressurized fluid and an inlet line connected to the source of pressurized fluid for fluid communication therebetween, the heart contracting device comprising:

an inflatable bladder including an outer wall and an inner wall, the inner wall being formed of substantially inelastic material, the bladder including an inlet port for releasable connection with the inlet line, the bladder being inflatable to drive the inner wall to a heart contracting position;

wherein the bladder comprises plural spaced apart inflatable compartments, and further comprising:

plural inlet lines, at least one of the lines being in communication with each of the respective compartments.

40. A heart contracting device for use in a system for assisting a heart to pump blood, the system including a source of pressurized fluid and an inlet line connected to the source of pressurized fluid for fluid communication therebetween, the heart contracting device comprising:

an inflatable bladder including an outer wall and an inner wall, the inner wall being formed of substantially inelastic material, the bladder including an inlet port for releasable connection with the inlet line, the bladder being inflatable to drive the inner wall to a heart contracting position;

further comprising at least two inlet lines, each of which is in fluid communication with the bladder at respective spaced apart locations.

41. A heart contracting device for use in a system for assisting a heart to pump blood, the system including a source of pressurized fluid and an inlet line connected to the source of pressurized fluid for fluid communication therebetween, the heart contracting device comprising:

an inflatable bladder including an outer wall and an inner wall, the inner wall being formed of substantially inelastic material, the bladder including an inlet port for releasable connection with the inlet line, the bladder being inflatable to drive the inner wall to a heart contracting position;

wherein the bladder is in the form of an elongated strip including first and second ends, the bladder being formed of a flexible material to be wrapped about the heart, the bladder further including a fastener device to secure the bladder in place about the heart.

42. An apparatus for assisting a heart to pump blood, the apparatus comprising:

a heart engaging device configured to releasably engage the heart;

a source of pressurized fluid; and a bladder formed of substantially inelastic, flexible material and adapted to be positioned about the periphery of at least a portion of the heart, the bladder being connectable to the source of pressurized fluid and inflatable to a heart compressing position to compress at least a portion of the heart;

wherein the bladder comprises plural inflatable compartments, and further including:

plural inlet lines, at least one of each being in communication with each of the respective compartments.

43. An apparatus for assisting a heart to pump blood, the apparatus comprising:

a heart engaging device configured to releasably engage the heart;

a source of pressurized fluid; and a bladder formed of substantially inelastic, flexible material and adapted to be positioned about the periphery of at least a portion of the heart, the bladder being connectable to the source of pressurized fluid and inflatable to a heart compressing position to compress at least a portion of the heart;

further comprising at least two inlet lines, each of which is in fluid communication with the bladder at respective spaced apart locations.

44. An apparatus for assisting a heart to pump blood, the apparatus comprising:

a heart engaging device configured to releasably engage the heart;

a source of pressurized fluid; and a bladder formed of substantially inelastic, flexible material and adapted to be positioned about the periphery of at least a portion of the heart, the bladder being connectable to the source of pressurized fluid and inflatable to a heart compressing position to compress at least a portion of the heart;

wherein the heart engaging device comprises a suction membrane configured to make a close fit about at least a portion of the heart, the heart engaging device further including a suction line in communication with an interior chamber of the suction membrane, the suction line being operative to create a vacuum in the chamber to draw the suction membrane inwardly and into engagement with the heart.

45. An apparatus for assisting a heart to pump blood, the apparatus comprising:

a heart engaging device configured to releasably engage at least a portion of the heart;

a source of pressurized fluid; and a bladder adapted to be positioned about the periphery of at least a portion of the heart, the bladder including an inner wall having a predetermined surface area such that the inner wall is at least partially folded when in a deflated state and at least partially unfolds when in an inflated state, the bladder being connectable to the source of pressurized fluid and inflatable to compress at least a portion of the heart;

further comprising at least two inlet lines, each of which is in fluid communication with the bladder at respective spaced apart locations.

46. An apparatus for assisting a heart to pump blood, the apparatus comprising:

a heart engaging device configured to releasably engage at least a portion of the heart;

a source of pressurized fluid; and a bladder adapted to be positioned about the periphery of at least a portion of the heart, the bladder including an inner wall having a predetermined surface area such that the inner wall is at least partially folded when in a deflated state and at least partially unfolds when in an inflated state, the bladder being connectable to the source of pressurized fluid and inflatable to compress at least a portion of the heart;

wherein the bladder is in the form of an elongated strip including first and second ends, the bladder being formed of a flexible material to be wrapped about the heart, the bladder further including a fastener device to secure the bladder in place about the heart.

47. An apparatus for assisting a heart to pump blood, the apparatus comprising:

a heart engaging device configured to releasably engage at least a portion of the heart;

a source of pressurized fluid; and a bladder adapted to be positioned about the periphery of at least a portion of the heart, the bladder including an inner wall having a predetermined surface area such that the inner wall is at least partially folded when in a deflated state and at least partially unfolds when in an inflated state, the bladder being connectable to the source of pressurized fluid and inflatable to compress at least a portion of the heart;

wherein the heart engaging device comprises a suction membrane configured to make a close fit about at least a portion of the heart, the heart engaging device further including a suction line in communication with an interior chamber of the suction membrane, the suction line being operative to create a vacuum in the chamber to draw the suction membrane inwardly and into engagement with the heart.

* * * * *